(12) United States Patent
McClurken

(10) Patent No.: US 7,951,148 B2
(45) Date of Patent: May 31, 2011

(54) ELECTROSURGICAL DEVICE HAVING A TISSUE REDUCTION SENSOR

(75) Inventor: Michael E. McClurken, Durham, NH (US)

(73) Assignee: Salient Surgical Technologies, Inc., Portsmouth, NH (US)

( * ) Notice: Subject to any disclaimer, the term of this patent is extended or adjusted under 35 U.S.C. 154(b) by 596 days.

(21) Appl. No.: 10/773,503

(22) Filed: Feb. 6, 2004

(65) Prior Publication Data

US 2004/0162552 A1  Aug. 19, 2004

Related U.S. Application Data

(63) Continuation of application No. 09/802,288, filed on Mar. 8, 2001, now Pat. No. 6,689,131.

(51) Int. Cl.
*A61B 18/14* (2006.01)

(52) U.S. Cl. ............... 606/51; 606/52; 606/48

(58) Field of Classification Search .......... 606/27, 606/40, 41, 31, 32; 600/373, 372; 604/104–107, 604/19–21, 93, 500, 113; 607/1, 2, 96, 101, 607/103, 122
See application file for complete search history.

(56) References Cited

U.S. PATENT DOCUMENTS

| 623,022 | A | 4/1899 | Johnson |
|---|---|---|---|
| 1,735,271 | A | 11/1929 | Groff |
| 1,814,791 | A | 7/1931 | Ende |
| 2,002,594 | A | 5/1935 | Wappler et al. |
| 2,031,682 | A | 2/1936 | Wappler et al. |
| 2,102,270 | A | 12/1937 | Hyams |
| 2,275,167 | A | 3/1942 | Bierman |
| 2,888,928 | A | 6/1959 | Seiger |
| 3,163,166 | A | 12/1964 | Brant et al. |
| 3,682,130 | A | 8/1972 | Jeffers |
| 3,750,650 | A | 8/1973 | Ruttgers |
| 3,901,241 | A | 8/1975 | Allen, Jr. |
| 4,037,590 | A | 7/1977 | Dohring et al. |
| 4,060,088 | A | 11/1977 | Morrison, Jr. et al. |
| 4,116,198 | A | 9/1978 | Roos |
| 4,244,371 | A | 1/1981 | Farin |
| 4,276,874 | A | 7/1981 | Wolvek et al. |

(Continued)

FOREIGN PATENT DOCUMENTS

EP  0 175 595 A1  3/1986

(Continued)

OTHER PUBLICATIONS

English language abstract for EP 0 175 575 A1, published Mar. 26, 1986, 1 page.

(Continued)

*Primary Examiner* — Michael Peffley
(74) *Attorney, Agent, or Firm* — Sterne, Kessler, Goldstein & Fox

(57) ABSTRACT

An electrosurgical device for use in surgical procedures is disclosed. The electrosurgical device comprises a main body having a proximal end and a distal end. A heat delivery modality is situated and arranged at the distal end of the main body. A sensor arrangement is also situated and arranged at the distal end of the main body. The heat delivery modality provides thermal energy to a tissue being treated while the sensor arrangement is configured to engage and detect a change in dimension of the tissue being treated. Accordingly, the electrosurgical device of the present disclosure allows a surgeon to precisely achieve the desired amount of dimensional change of the tissue being treated.

31 Claims, 10 Drawing Sheets

U.S. PATENT DOCUMENTS

| | | | |
|---|---|---|---|
| 4,301,802 A | 11/1981 | Poler | |
| 4,307,720 A | 12/1981 | Weber, Jr. | |
| 4,321,931 A | 3/1982 | Hon | |
| 4,326,529 A | 4/1982 | Doss et al. | |
| 4,342,218 A | 8/1982 | Fox | |
| 4,355,642 A | 10/1982 | Alferness | |
| 4,381,007 A | 4/1983 | Doss | |
| 4,532,924 A | 8/1985 | Auth et al. | |
| 4,548,207 A | 10/1985 | Reimels | |
| 4,567,890 A | 2/1986 | Ohta et al. | |
| 4,602,628 A | 7/1986 | Allen, Jr. | |
| 4,671,274 A | 6/1987 | Sorochenko | |
| 4,674,499 A | 6/1987 | Pao | |
| 4,920,982 A | 5/1990 | Goldstein | |
| 4,931,047 A | 6/1990 | Broadwin et al. | |
| 4,932,952 A | 6/1990 | Wojciechowicz, Jr. | |
| 4,943,290 A | 7/1990 | Rexroth et al. | |
| 4,950,232 A | 8/1990 | Ruzicka et al. | |
| 4,976,711 A | 12/1990 | Parins et al. | |
| 4,985,030 A | 1/1991 | Melzer et al. | |
| 4,998,933 A | 3/1991 | Eggers et al. | |
| 5,009,656 A | 4/1991 | Reimels | |
| 5,013,312 A | 5/1991 | Parins et al. | |
| 5,035,696 A | 7/1991 | Rydell | |
| 5,071,419 A | 12/1991 | Rydell et al. | |
| 5,080,660 A | 1/1992 | Buelna | |
| 5,122,138 A | 6/1992 | Manwaring | |
| 5,125,928 A | 6/1992 | Parins et al. | |
| 5,147,357 A | 9/1992 | Rose et al. | |
| 5,151,102 A | 9/1992 | Kamiyama et al. | |
| 5,156,613 A | 10/1992 | Sawyer | |
| 5,167,659 A | 12/1992 | Ohtomo et al. | |
| 5,171,311 A | 12/1992 | Rydell et al. | |
| 5,190,541 A | 3/1993 | Abele et al. | |
| 5,195,959 A | 3/1993 | Smith | |
| 5,197,963 A | 3/1993 | Parins | |
| 5,197,964 A | 3/1993 | Parins | |
| 5,217,460 A | 6/1993 | Knoepfler | |
| 5,234,428 A | 8/1993 | Kaufman | |
| 5,242,441 A | 9/1993 | Avitall | |
| 5,242,442 A | 9/1993 | Hirschfeld | |
| 5,269,780 A | 12/1993 | Roos | |
| 5,269,781 A | 12/1993 | Hewell, III | |
| 5,277,696 A | 1/1994 | Hagen | |
| 5,281,215 A | 1/1994 | Milder | |
| 5,281,216 A | 1/1994 | Klicek | |
| 5,282,799 A | 2/1994 | Rydell | |
| 5,290,286 A | 3/1994 | Parins | |
| 5,300,087 A | 4/1994 | Knoepfler | |
| 5,313,943 A | 5/1994 | Houser et al. | |
| 5,318,589 A | 6/1994 | Lichtman | |
| 5,322,503 A | 6/1994 | Desai | |
| 5,330,521 A | 7/1994 | Cohen | |
| 5,334,193 A | 8/1994 | Nardella | |
| 5,342,357 A | 8/1994 | Nardella | |
| 5,342,359 A | 8/1994 | Rydell | |
| 5,348,554 A | 9/1994 | Imran et al. | |
| 5,364,394 A | 11/1994 | Mehl | |
| 5,383,874 A | 1/1995 | Jackson et al. | |
| 5,383,876 A | 1/1995 | Nardella | |
| 5,395,312 A | 3/1995 | Desai | |
| 5,395,363 A | 3/1995 | Billings et al. | |
| 5,401,272 A | 3/1995 | Perkins | |
| 5,403,311 A | 4/1995 | Abele et al. | |
| 5,403,312 A | 4/1995 | Yates et al. | |
| 5,405,344 A | 4/1995 | Williamson et al. | |
| 5,405,376 A | 4/1995 | Mulier et al. | |
| 5,417,672 A | 5/1995 | Nita et al. | |
| 5,417,709 A | 5/1995 | Slater | |
| 5,431,168 A | 7/1995 | Webster, Jr. | |
| 5,431,649 A | 7/1995 | Mulier et al. | |
| 5,433,708 A | 7/1995 | Nichols et al. | |
| 5,437,662 A | 8/1995 | Nardella | |
| 5,437,664 A | 8/1995 | Cohen et al. | |
| 5,441,498 A | 8/1995 | Perkins | |
| 5,441,503 A | 8/1995 | Considine et al. | |
| 5,445,638 A | 8/1995 | Rydell et al. | |
| 5,456,682 A | 10/1995 | Edwards et al. | |
| 5,456,684 A | 10/1995 | Schmidt et al. | |
| 5,458,596 A | 10/1995 | Lax et al. | |
| 5,458,597 A | 10/1995 | Edwards et al. | |
| 5,458,598 A | 10/1995 | Feinberg et al. | |
| 5,460,629 A | 10/1995 | Shlain et al. | |
| 5,462,521 A | 10/1995 | Brucker et al. | |
| 5,472,441 A | 12/1995 | Edwards et al. | |
| 5,472,443 A | 12/1995 | Cordis et al. | |
| 5,487,385 A | 1/1996 | Avitall | |
| 5,490,819 A | 2/1996 | Nicholas et al. | |
| 5,500,012 A | 3/1996 | Brucker et al. | |
| 5,514,130 A | 5/1996 | Baker | |
| 5,522,815 A | 6/1996 | Durgin, Jr. et al. | |
| 5,536,267 A | 7/1996 | Edwards et al. | |
| 5,540,562 A | 7/1996 | Giter | |
| 5,542,928 A | 8/1996 | Evans et al. | |
| 5,542,945 A | 8/1996 | Fritzsch | |
| 5,558,671 A | 9/1996 | Yates | |
| 5,562,503 A | 10/1996 | Ellman et al. | |
| 5,562,702 A * | 10/1996 | Huitema et al. | 606/207 |
| 5,562,703 A | 10/1996 | Desai | |
| 5,564,440 A | 10/1996 | Swartz et al. | |
| 5,569,242 A | 10/1996 | Lax et al. | |
| 5,569,243 A | 10/1996 | Kortenbach et al. | |
| 5,573,424 A | 11/1996 | Poppe | |
| 5,573,533 A | 11/1996 | Strul | |
| 5,575,810 A | 11/1996 | Swanson et al. | |
| 5,584,872 A | 12/1996 | LaFontaine et al. | |
| 5,599,346 A | 2/1997 | Edwards et al. | |
| 5,599,350 A | 2/1997 | Schulze et al. | |
| 5,605,539 A | 2/1997 | Buelna et al. | |
| 5,609,151 A | 3/1997 | Mulier et al. | |
| 5,633,578 A | 5/1997 | Eggers et al. | |
| 5,637,110 A | 6/1997 | Pennybacker et al. | |
| 5,640,955 A | 6/1997 | Ockuly et al. | |
| 5,643,197 A | 7/1997 | Brucker et al. | |
| 5,647,869 A | 7/1997 | Goble et al. | |
| 5,647,871 A | 7/1997 | Levine et al. | |
| 5,653,692 A | 8/1997 | Masterson et al. | |
| 5,660,836 A | 8/1997 | Knowlton | |
| 5,676,662 A | 10/1997 | Fleischhacker et al. | |
| 5,676,693 A | 10/1997 | LaFontaine | |
| 5,681,282 A | 10/1997 | Eggers et al. | |
| 5,683,366 A | 11/1997 | Eggers et al. | |
| 5,683,384 A | 11/1997 | Gough et al. | |
| 5,687,723 A | 11/1997 | Avitall | |
| 5,688,270 A | 11/1997 | Yates et al. | |
| 5,693,045 A | 12/1997 | Eggers | |
| 5,697,281 A | 12/1997 | Eggers et al. | |
| 5,697,536 A | 12/1997 | Eggers et al. | |
| 5,697,882 A | 12/1997 | Eggers et al. | |
| 5,697,909 A | 12/1997 | Eggers et al. | |
| 5,697,927 A | 12/1997 | Imran et al. | |
| 5,702,386 A | 12/1997 | Stern et al. | |
| 5,709,680 A | 1/1998 | Yates et al. | |
| 5,713,896 A | 2/1998 | Nardella | |
| 5,718,241 A | 2/1998 | Ben-Haim et al. | |
| 5,718,701 A | 2/1998 | Shai et al. | |
| 5,718,703 A | 2/1998 | Chin | |
| 5,722,400 A | 3/1998 | Ockuly et al. | |
| 5,725,524 A | 3/1998 | Mulier et al. | |
| 5,730,127 A | 3/1998 | Avitall | |
| 5,735,846 A | 4/1998 | Panescu et al. | |
| 5,743,903 A | 4/1998 | Stern et al. | |
| 5,746,739 A | 5/1998 | Sutter | |
| 5,749,869 A | 5/1998 | Lindenmeier et al. | |
| 5,755,717 A | 5/1998 | Yates et al. | |
| 5,755,753 A | 5/1998 | Knowlton | |
| 5,766,153 A | 6/1998 | Eggers et al. | |
| 5,766,167 A | 6/1998 | Eggers et al. | |
| 5,785,705 A | 7/1998 | Baker | |
| 5,785,706 A | 7/1998 | Bednarek | |
| 5,792,140 A | 8/1998 | Tu et al. | |
| 5,797,905 A | 8/1998 | Fleischman et al. | |
| 5,797,960 A | 8/1998 | Stevens et al. | |
| 5,800,413 A | 9/1998 | Swartz et al. | |
| 5,800,482 A | 9/1998 | Pomeranz | |
| 5,807,393 A | 9/1998 | Williamson et al. | |
| 5,807,395 A | 9/1998 | Mulier et al. | |

| | | | |
|---|---|---|---|
| 5,810,764 A | 9/1998 | Eggers et al. |
| 5,810,805 A | 9/1998 | Sutcu et al. |
| 5,810,811 A | 9/1998 | Yates et al. |
| 5,817,093 A | 10/1998 | Williamson et al. |
| 5,823,956 A | 10/1998 | Roth et al. |
| 5,827,271 A | 10/1998 | Buysse et al. |
| 5,827,281 A | 10/1998 | Levin |
| 5,833,703 A | 11/1998 | Manushakian |
| 5,843,019 A | 12/1998 | Eggers et al. |
| 5,843,021 A | 12/1998 | Edwards et al. |
| 5,843,078 A | 12/1998 | Sharkey |
| 5,843,152 A | 12/1998 | Tu et al. |
| 5,855,614 A | 1/1999 | Stevens et al. |
| 5,860,951 A | 1/1999 | Eggers et al. |
| 5,860,974 A | 1/1999 | Abele |
| 5,861,002 A | 1/1999 | Desai |
| 5,861,021 A | 1/1999 | Thome et al. |
| 5,868,739 A | 2/1999 | Lindenmeier et al. |
| 5,871,469 A | 2/1999 | Eggers et al. |
| 5,871,524 A | 2/1999 | Knowlton |
| 5,873,855 A | 2/1999 | Eggers et al. |
| 5,876,398 A | 3/1999 | Mulier et al. |
| 5,888,198 A | 3/1999 | Eggers et al. |
| 5,891,095 A | 4/1999 | Eggers et al. |
| 5,891,141 A | 4/1999 | Rydell |
| 5,891,142 A | 4/1999 | Eggers et al. |
| 5,893,848 A * | 4/1999 | Negus et al. .................. 606/41 |
| 5,895,355 A | 4/1999 | Schaer |
| 5,895,417 A | 4/1999 | Pomeranz et al. |
| 5,897,553 A | 4/1999 | Mulier et al. |
| 5,902,272 A | 5/1999 | Eggers et al. |
| 5,902,328 A | 5/1999 | LaFontaine et al. |
| 5,904,711 A | 5/1999 | Flom et al. |
| 5,906,613 A | 5/1999 | Mulier et al. |
| 5,913,854 A | 6/1999 | Maguire et al. |
| 5,913,856 A | 6/1999 | Chia et al. |
| 5,919,191 A | 7/1999 | Lennox et al. |
| 5,919,219 A | 7/1999 | Knowlton |
| 5,921,982 A | 7/1999 | Lesh et al. |
| 5,921,983 A | 7/1999 | Shannon, Jr. |
| 5,925,045 A | 7/1999 | Reimels et al. |
| 5,935,123 A | 8/1999 | Edwards et al. |
| 5,948,011 A | 9/1999 | Knowlton |
| 5,951,549 A | 9/1999 | Richardson et al. |
| 5,954,716 A | 9/1999 | Sharkey et al. |
| 5,957,919 A | 9/1999 | Laufer |
| 5,964,755 A | 10/1999 | Edwards |
| 5,971,983 A | 10/1999 | Lesh |
| 5,976,128 A | 11/1999 | Schilling et al. |
| 5,980,504 A | 11/1999 | Sharkey et al. |
| 5,980,516 A | 11/1999 | Mulier et al. |
| 5,989,248 A | 11/1999 | Tu et al. |
| 5,992,418 A | 11/1999 | de la Rama et al. |
| 5,993,412 A | 11/1999 | Deily et al. |
| 6,003,517 A | 12/1999 | Sheffield et al. |
| 6,004,316 A | 12/1999 | Laufer |
| 6,004,319 A | 12/1999 | Goble et al. |
| 6,007,570 A | 12/1999 | Sharkey et al. |
| 6,010,500 A | 1/2000 | Sherman et al. |
| 6,015,391 A | 1/2000 | Rishton et al. |
| 6,015,407 A | 1/2000 | Rieb et al. |
| 6,016,809 A | 1/2000 | Mulier et al. |
| 6,017,338 A | 1/2000 | Brucker et al. |
| 6,018,676 A | 1/2000 | Davis et al. |
| 6,019,757 A | 2/2000 | Scheldrup |
| 6,024,733 A | 2/2000 | Eggers et al. |
| 6,027,501 A | 2/2000 | Goble et al. |
| 6,030,379 A | 2/2000 | Panescu et al. |
| 6,032,077 A | 2/2000 | Pomeranz |
| 6,032,674 A * | 3/2000 | Eggers et al. ............... 128/898 |
| 6,033,398 A * | 3/2000 | Farley et al. ................. 606/27 |
| 6,035,238 A | 3/2000 | Ingle et al. |
| 6,036,687 A | 3/2000 | Laufer et al. |
| 6,045,532 A | 4/2000 | Eggers et al. |
| 6,047,700 A | 4/2000 | Eggers et al. |
| 6,048,333 A | 4/2000 | Lennox et al. |
| 6,053,172 A | 4/2000 | Hovda et al. |
| 6,053,912 A | 4/2000 | Panescu et al. |
| 6,056,744 A | 5/2000 | Edwards |
| 6,056,745 A | 5/2000 | Panescu et al. |
| 6,056,747 A | 5/2000 | Saadat et al. |
| 6,059,781 A | 5/2000 | Yamanashi et al. |
| 6,063,079 A | 5/2000 | Hovda et al. |
| 6,063,081 A | 5/2000 | Mulier et al. |
| 6,066,134 A | 5/2000 | Eggers et al. |
| 6,066,139 A | 5/2000 | Ryan et al. |
| 6,068,627 A | 5/2000 | Orszulak et al. |
| 6,068,653 A | 5/2000 | LaFontaine |
| 6,071,280 A | 6/2000 | Edwards et al. |
| 6,073,051 A | 6/2000 | Sharkey et al. |
| 6,074,389 A | 6/2000 | Levine et al. |
| 6,080,151 A | 6/2000 | Swartz et al. |
| 6,081,749 A | 6/2000 | Ingle et al. |
| 6,083,237 A | 7/2000 | Huitema et al. |
| 6,086,585 A | 7/2000 | Hovda et al. |
| 6,086,586 A | 7/2000 | Hooven |
| 6,091,995 A | 7/2000 | Ingle et al. |
| 6,093,186 A | 7/2000 | Goble |
| 6,095,149 A | 8/2000 | Sharkey et al. |
| 6,096,037 A * | 8/2000 | Mulier et al. .................. 606/49 |
| 6,099,514 A | 8/2000 | Sharkey et al. |
| 6,102,046 A | 8/2000 | Weinstein et al. |
| 6,105,581 A | 8/2000 | Eggers et al. |
| 6,109,268 A | 8/2000 | Thapliyal et al. |
| 6,113,596 A | 9/2000 | Hooven et al. |
| 6,113,597 A | 9/2000 | Eggers et al. |
| 6,117,109 A | 9/2000 | Eggers et al. |
| 6,122,549 A | 9/2000 | Sharkey et al. |
| H1904 H | 10/2000 | Yates et al. |
| 6,126,682 A | 10/2000 | Sharkey et al. |
| 6,135,999 A | 10/2000 | Fanton et al. |
| 6,141,576 A | 10/2000 | Littmann et al. |
| 6,142,992 A | 11/2000 | Cheng et al. |
| 6,149,620 A | 11/2000 | Baker et al. |
| 6,159,194 A | 12/2000 | Eggers et al. |
| 6,159,208 A | 12/2000 | Hovda et al. |
| 6,165,169 A | 12/2000 | Panescu et al. |
| 6,165,175 A | 12/2000 | Wampler et al. |
| 6,168,594 B1 | 1/2001 | LaFontaine et al. |
| 6,171,275 B1 | 1/2001 | Webster, Jr. |
| 6,174,308 B1 | 1/2001 | Goble et al. |
| 6,174,309 B1 | 1/2001 | Wrubleski et al. |
| 6,176,857 B1 | 1/2001 | Ashley |
| 6,179,824 B1 | 1/2001 | Eggers et al. |
| 6,179,836 B1 | 1/2001 | Eggers et al. |
| 6,183,469 B1 | 2/2001 | Thapliyal et al. |
| 6,190,381 B1 | 2/2001 | Olsen et al. |
| 6,190,384 B1 | 2/2001 | Ouchi |
| 6,193,715 B1 | 2/2001 | Wrubleski et al. |
| 6,193,716 B1 | 2/2001 | Shannon, Jr. |
| 6,203,542 B1 | 3/2001 | Ellsberry et al. |
| 6,210,402 B1 | 4/2001 | Olsen et al. |
| 6,210,410 B1 | 4/2001 | Farin et al. |
| 6,210,411 B1 | 4/2001 | Hofmann et al. |
| 6,212,426 B1 | 4/2001 | Swanson |
| 6,216,704 B1 * | 4/2001 | Ingle et al. .................. 128/898 |
| 6,217,576 B1 | 4/2001 | Tu et al. |
| 6,221,039 B1 | 4/2001 | Durgin et al. |
| 6,221,069 B1 | 4/2001 | Daikuzono |
| 6,224,592 B1 | 5/2001 | Eggers et al. |
| 6,224,593 B1 | 5/2001 | Ryan et al. |
| 6,226,554 B1 | 5/2001 | Tu et al. |
| 6,228,078 B1 | 5/2001 | Eggers et al. |
| 6,228,082 B1 | 5/2001 | Baker et al. |
| 6,231,591 B1 | 5/2001 | Desai |
| 6,235,020 B1 | 5/2001 | Cheng et al. |
| 6,236,891 B1 | 5/2001 | Ingle et al. |
| 6,238,387 B1 | 5/2001 | Miller, III |
| 6,238,391 B1 | 5/2001 | Olsen et al. |
| 6,238,393 B1 | 5/2001 | Mulier et al. |
| 6,241,753 B1 | 6/2001 | Knowlton |
| 6,241,754 B1 | 6/2001 | Swanson et al. |
| 6,251,110 B1 | 6/2001 | Wampler |
| 6,254,600 B1 | 7/2001 | Willink et al. |
| 6,258,086 B1 | 7/2001 | Ashley et al. |
| 6,258,087 B1 | 7/2001 | Edwards et al. |
| 6,261,311 B1 | 7/2001 | Sharkey et al. |
| 6,264,650 B1 | 7/2001 | Hovda et al. |

| Patent No. | Date | Inventor |
|---|---|---|
| 6,264,651 B1 | 7/2001 | Underwood et al. |
| 6,264,652 B1 | 7/2001 | Eggers et al. |
| 6,264,654 B1 | 7/2001 | Swartz et al. |
| 6,266,551 B1 | 7/2001 | Osadchy et al. |
| 6,277,112 B1 | 8/2001 | Underwood et al. |
| 6,280,440 B1 | 8/2001 | Gocho |
| 6,283,961 B1 | 9/2001 | Underwood et al. |
| 6,283,988 B1 | 9/2001 | Laufer et al. |
| 6,283,989 B1 | 9/2001 | Laufer et al. |
| 6,290,715 B1 | 9/2001 | Sharkey et al. |
| 6,293,942 B1 | 9/2001 | Goble et al. |
| 6,293,945 B1 | 9/2001 | Parins et al. |
| 6,296,636 B1 | 10/2001 | Cheng et al. |
| 6,296,638 B1 | 10/2001 | Davison et al. |
| 6,296,640 B1 | 10/2001 | Wampler et al. |
| 6,299,633 B1 | 10/2001 | Laufer |
| 6,302,903 B1 | 10/2001 | Mulier et al. |
| 6,306,134 B1 | 10/2001 | Goble et al. |
| 6,309,387 B1 | 10/2001 | Eggers et al. |
| 6,311,090 B1 | 10/2001 | Knowlton |
| 6,312,408 B1 | 11/2001 | Eggers et al. |
| 6,312,430 B1 | 11/2001 | Wilson et al. |
| 6,315,777 B1 | 11/2001 | Comben |
| 6,322,549 B1 | 11/2001 | Eggers et al. |
| 6,322,559 B1 | 11/2001 | Daulton et al. |
| 6,327,505 B1 | 12/2001 | Medhkour et al. |
| 6,328,735 B1 | 12/2001 | Curley et al. |
| 6,328,736 B1 | 12/2001 | Mulier et al. |
| 6,336,926 B1 | 1/2002 | Goble |
| 6,350,262 B1 | 2/2002 | Ashley |
| 6,350,276 B1 | 2/2002 | Knowlton |
| 6,352,533 B1 | 3/2002 | Ellman et al. |
| 6,355,032 B1 | 3/2002 | Hovda et al. |
| 6,358,245 B1 | 3/2002 | Edwards et al. |
| 6,358,248 B1 | 3/2002 | Mulier et al. |
| 6,363,937 B1 | 4/2002 | Hovda et al. |
| 6,371,956 B1 | 4/2002 | Wilson et al. |
| 6,379,350 B1 | 4/2002 | Sharkey et al. |
| 6,379,351 B1 | 4/2002 | Thapliyal et al. |
| 6,391,025 B1 | 5/2002 | Weinstein et al. |
| 6,391,028 B1 | 5/2002 | Fanton et al. |
| 6,402,742 B1 | 6/2002 | Blewett et al. |
| 6,409,722 B1 | 6/2002 | Hoey et al. |
| 6,409,723 B1 | 6/2002 | Edwards |
| H2037 H | 7/2002 | Yates et al. |
| 6,416,507 B1 | 7/2002 | Eggers et al. |
| 6,416,508 B1 | 7/2002 | Eggers et al. |
| 6,416,509 B1 | 7/2002 | Goble et al. |
| 6,425,877 B1 | 7/2002 | Edwards |
| 6,432,103 B1 | 8/2002 | Ellsberry et al. |
| 6,440,130 B1 | 8/2002 | Mulier et al. |
| 6,443,952 B1 | 9/2002 | Mulier et al. |
| 6,451,017 B1 | 9/2002 | Moutafis et al. |
| 6,458,123 B1 | 10/2002 | Brucker et al. |
| 6,458,130 B1 | 10/2002 | Frazier et al. |
| 6,461,350 B1 | 10/2002 | Underwood et al. |
| 6,461,354 B1 | 10/2002 | Olsen et al. |
| 6,461,357 B1 | 10/2002 | Sharkey et al. |
| 6,464,695 B2 | 10/2002 | Hovda et al. |
| 6,468,270 B1 | 10/2002 | Hovda et al. |
| 6,468,274 B1 | 10/2002 | Alleyne et al. |
| 6,468,275 B1 | 10/2002 | Wampler et al. |
| 6,471,698 B1 | 10/2002 | Edwards et al. |
| 6,475,216 B2 | 11/2002 | Mulier et al. |
| 6,478,793 B1 | 11/2002 | Cosman et al. |
| 6,482,202 B1 | 11/2002 | Goble et al. |
| 6,485,490 B2 | 11/2002 | Wampler et al. |
| 6,488,680 B1 | 12/2002 | Francischelli et al. |
| 6,493,589 B1 | 12/2002 | Medhkour et al. |
| 6,494,902 B2 | 12/2002 | Hoey et al. |
| 6,497,704 B2 | 12/2002 | Ein-Gal |
| 6,497,705 B2 | 12/2002 | Comben |
| 6,506,189 B1 | 1/2003 | Rittman, III et al. |
| 6,508,815 B1 | 1/2003 | Strul et al. |
| 6,517,536 B2 | 2/2003 | Hooven et al. |
| 6,526,320 B2 | 2/2003 | Mitchell |
| 6,537,248 B2 | 3/2003 | Mulier et al. |
| 6,537,272 B2 | 3/2003 | Christopherson et al. |
| 6,539,265 B2 | 3/2003 | Medhkour et al. |
| 6,558,379 B1 | 5/2003 | Batchelor et al. |
| 6,558,385 B1 | 5/2003 | McClurken et al. |
| 6,575,969 B1 | 6/2003 | Rittman, III et al. |
| 6,577,902 B1 | 6/2003 | Laufer et al. |
| 6,579,288 B1 | 6/2003 | Swanson et al. |
| 6,585,732 B2 | 7/2003 | Mulier et al. |
| 6,602,248 B1 | 8/2003 | Sharps et al. |
| 6,603,988 B2 | 8/2003 | Dowlatshahi |
| 6,610,060 B2 | 8/2003 | Mulier et al. |
| 6,613,048 B2 | 9/2003 | Mulier et al. |
| 6,623,515 B2 | 9/2003 | Mulier et al. |
| 6,626,899 B2 | 9/2003 | Houser et al. |
| 6,645,202 B1 * | 11/2003 | Pless et al. ........... 606/41 |
| 6,666,862 B2 | 12/2003 | Jain et al. |
| 6,669,692 B1 | 12/2003 | Nelson et al. |
| 6,676,660 B2 | 1/2004 | Wampler |
| 6,679,882 B1 | 1/2004 | Kornerup |
| 6,682,501 B1 | 1/2004 | Nelson et al. |
| 6,682,527 B2 | 1/2004 | Strul |
| 6,682,528 B2 | 1/2004 | Fraizer et al. |
| 6,685,700 B2 | 2/2004 | Behl et al. |
| 6,685,701 B2 | 2/2004 | Orszulak et al. |
| 6,685,704 B2 | 2/2004 | Greep |
| 6,689,129 B2 | 2/2004 | Baker |
| 6,689,131 B2 | 2/2004 | McClurken |
| 6,692,489 B1 | 2/2004 | Heim et al. |
| 6,694,984 B2 | 2/2004 | Habib |
| 6,695,837 B2 | 2/2004 | Howell |
| 6,695,840 B2 | 2/2004 | Schulze |
| 6,699,240 B2 | 3/2004 | Francischelli |
| 6,699,242 B2 | 3/2004 | Heggeness |
| 6,699,244 B2 | 3/2004 | Carranza et al. |
| 6,699,268 B2 | 3/2004 | Kordis et al. |
| 6,702,810 B2 | 3/2004 | McClurken et al. |
| 6,702,812 B2 | 3/2004 | Cosmescu |
| 6,706,039 B2 | 3/2004 | Mulier et al. |
| 6,712,074 B2 | 3/2004 | Edwards et al. |
| 6,712,811 B2 | 3/2004 | Underwood et al. |
| 6,712,813 B2 | 3/2004 | Ellman et al. |
| 6,712,816 B2 | 3/2004 | Hung et al. |
| 6,716,211 B2 | 4/2004 | Mulier et al. |
| 6,719,754 B2 | 4/2004 | Underwood et al. |
| 6,723,094 B1 | 4/2004 | Desinger |
| 6,726,683 B1 | 4/2004 | Shaw |
| 6,726,684 B1 | 4/2004 | Woloszko et al. |
| 6,726,686 B2 | 4/2004 | Buysse et al. |
| 6,730,081 B1 | 5/2004 | Desai |
| 6,733,496 B2 | 5/2004 | Sharkey et al. |
| 6,733,498 B2 | 5/2004 | Paton et al. |
| 6,733,501 B2 | 5/2004 | Levine |
| 6,736,810 B2 | 5/2004 | Hoey et al. |
| 6,740,058 B2 | 5/2004 | Lal et al. |
| 6,740,079 B1 | 5/2004 | Eggers et al. |
| 6,740,082 B2 | 5/2004 | Shadduck |
| 6,740,084 B2 | 5/2004 | Ryan |
| 6,740,102 B2 | 5/2004 | Hess et al. |
| 6,743,197 B1 | 6/2004 | Edwards |
| 6,743,229 B2 | 6/2004 | Buysse et al. |
| 6,743,230 B2 | 6/2004 | Lutze et al. |
| 6,746,447 B2 | 6/2004 | Davison et al. |
| 6,755,825 B2 | 6/2004 | Shoenman et al. |
| 6,755,827 B2 | 6/2004 | Mulier et al. |
| 6,757,565 B2 | 6/2004 | Sharkey et al. |
| 6,758,846 B2 | 7/2004 | Goble et al. |
| 6,761,718 B2 | 7/2004 | Madsen |
| 6,764,487 B2 | 7/2004 | Mulier et al. |
| 6,766,817 B2 | 7/2004 | da Silva |
| 6,770,070 B1 | 8/2004 | Balbierz |
| 6,770,071 B2 | 8/2004 | Woloszko et al. |
| 6,770,072 B1 | 8/2004 | Truckai et al. |
| 6,772,012 B2 | 8/2004 | Ricart et al. |
| 6,772,013 B1 | 8/2004 | Ingle et al. |
| 6,775,575 B2 * | 8/2004 | Bommannan et al. ........ 607/101 |
| 6,776,780 B2 | 8/2004 | Mulier et al. |
| 6,780,177 B2 | 8/2004 | Shafirstein et al. |
| 6,780,180 B1 | 8/2004 | Goble et al. |
| 6,786,906 B1 | 9/2004 | Cobb |
| 6,796,981 B2 | 9/2004 | Wham et al. |
| 6,800,077 B1 | 10/2004 | Mucko et al. |

| | | |
|---|---|---|
| 6,802,842 B2 | 10/2004 | Ellman et al. |
| 6,802,843 B2 | 10/2004 | Truckai et al. |
| 6,808,525 B2 | 10/2004 | Latterell et al. |
| 6,813,520 B2 | 11/2004 | Truckai et al. |
| 6,814,714 B1 | 11/2004 | Novak et al. |
| 6,814,731 B2 | 11/2004 | Swanson |
| 6,821,273 B2 | 11/2004 | Mollenauer |
| 6,827,713 B2 | 12/2004 | Bek et al. |
| 6,827,725 B2 | 12/2004 | Batchelor et al. |
| 6,832,997 B2 | 12/2004 | Uchida et al. |
| 6,835,195 B2 | 12/2004 | Schulze et al. |
| 6,836,688 B2 | 12/2004 | Ingle et al. |
| 6,843,789 B2 | 1/2005 | Goble |
| 6,845,264 B1 | 1/2005 | Skladnev et al. |
| 6,849,073 B2 | 2/2005 | Hoey et al. |
| 6,855,145 B2 | 2/2005 | Ciarrocca |
| 6,858,028 B2 | 2/2005 | Mulier et al. |
| 6,860,882 B2 | 3/2005 | Battles et al. |
| 6,863,669 B2 | 3/2005 | Spitzer |
| 6,864,686 B2 | 3/2005 | Novak et al. |
| 6,881,214 B2 | 4/2005 | Cosman et al. |
| 6,882,885 B2 | 4/2005 | Levy, Jr. et al. |
| 6,887,237 B2 | 5/2005 | McGaffigan |
| 6,887,240 B1 | 5/2005 | Lands et al. |
| 6,893,435 B2 | 5/2005 | Goble |
| 6,893,440 B2 | 5/2005 | Durgin et al. |
| 6,896,672 B1 | 5/2005 | Eggers et al. |
| 6,896,674 B1 | 5/2005 | Woloszko et al. |
| 6,899,712 B2 | 5/2005 | Moutafis et al. |
| 6,905,497 B2 | 6/2005 | Truckai et al. |
| 6,905,499 B1 | 6/2005 | Mucko et al. |
| 6,911,019 B2 | 6/2005 | Mulier et al. |
| 6,915,806 B2 | 7/2005 | Pacek et al. |
| 6,918,404 B2 | 7/2005 | Dias da Silva |
| 6,921,398 B2 | 7/2005 | Carmel et al. |
| 6,921,399 B2 | 7/2005 | Carmel et al. |
| 6,923,803 B2 | 8/2005 | Goble |
| 6,923,805 B1 | 8/2005 | LaFontaine et al. |
| 6,926,706 B1 | 8/2005 | Sealfon |
| 6,926,716 B2 | 8/2005 | Baker et al. |
| 6,926,717 B1 | 8/2005 | Garito et al. |
| 6,929,640 B1 | 8/2005 | Underwood et al. |
| 6,929,641 B2 | 8/2005 | Goble et al. |
| 6,929,642 B2 | 8/2005 | Xiao et al. |
| 6,929,644 B2 | 8/2005 | Truckai et al. |
| 6,929,645 B2 | 8/2005 | Battles et al. |
| 6,932,810 B2 | 8/2005 | Ryan |
| 6,932,815 B2 | 8/2005 | Sutter |
| 6,942,661 B2 | 9/2005 | Swanson |
| 6,949,096 B2 | 9/2005 | Davison et al. |
| 6,949,098 B2 | 9/2005 | Mulier et al. |
| 6,951,559 B1 | 10/2005 | Greep |
| 6,953,461 B2 | 10/2005 | McClurken et al. |
| 6,960,204 B2 | 11/2005 | Eggers et al. |
| 6,960,207 B2 | 11/2005 | Vanney et al. |
| 6,960,210 B2 | 11/2005 | Lands et al. |
| 6,962,589 B2 | 11/2005 | Mulier et al. |
| 6,964,274 B1 | 11/2005 | Ryan et al. |
| 6,964,661 B2 | 11/2005 | Rioux et al. |
| 6,966,907 B2 | 11/2005 | Goble |
| 6,966,909 B2 | 11/2005 | Marshall et al. |
| 6,971,394 B2 | 12/2005 | Sliwa, Jr. et al. |
| 6,974,452 B1 | 12/2005 | Gille et al. |
| 6,974,453 B2 | 12/2005 | Woloszko et al. |
| 6,979,332 B2 | 12/2005 | Adams |
| 6,984,231 B2 | 1/2006 | Goble et al. |
| 6,986,769 B2 | 1/2006 | Nelson et al. |
| 6,991,631 B2 | 1/2006 | Woloszko et al. |
| 7,001,380 B2 | 2/2006 | Goble |
| 7,001,382 B2 | 2/2006 | Gallo, Sr. |
| 7,004,941 B2 | 2/2006 | Tvinnereim et al. |
| 7,004,942 B2 | 2/2006 | Laird et al. |
| 7,008,419 B2 | 3/2006 | Shadduck |
| 7,008,421 B2 | 3/2006 | Daniel et al. |
| 7,033,348 B2 | 4/2006 | Alfano et al. |
| 7,033,356 B2 | 4/2006 | Latterell et al. |
| 7,041,096 B2 | 5/2006 | Malis et al. |
| 7,041,101 B2 | 5/2006 | Eggers |
| 7,041,102 B2 | 5/2006 | Truckai et al. |
| 7,052,494 B2 | 5/2006 | Goble et al. |
| 7,060,064 B2 | 6/2006 | Allen et al. |
| 7,063,670 B2 | 6/2006 | Sampson et al. |
| 7,066,586 B2 | 6/2006 | da Silva |
| 7,066,932 B1 | 6/2006 | Morgan et al. |
| 7,066,936 B2 | 6/2006 | Ryan |
| 7,070,596 B1 | 7/2006 | Woloszko et al. |
| 7,070,604 B1 | 7/2006 | Garito et al. |
| 7,074,217 B2 | 7/2006 | Strul et al. |
| 7,074,219 B2 | 7/2006 | Levine et al. |
| 7,083,601 B1 | 8/2006 | Cosmescu |
| 7,087,051 B2 | 8/2006 | Bourne et al. |
| 7,087,053 B2 | 8/2006 | Vanney |
| 7,094,215 B2 | 8/2006 | Davison et al. |
| 7,101,387 B2 | 9/2006 | Garabedian et al. |
| 7,104,986 B2 | 9/2006 | Hovda et al. |
| 7,112,199 B2 | 9/2006 | Cosmescu |
| 7,115,139 B2 | 10/2006 | McClurken et al. |
| 7,125,406 B2 | 10/2006 | Given |
| 7,147,634 B2 | 12/2006 | Nesbitt |
| 7,147,635 B2 | 12/2006 | Ciarrocca |
| 7,147,637 B2 | 12/2006 | Goble |
| 7,147,638 B2 | 12/2006 | Chapman et al. |
| 7,150,746 B2 | 12/2006 | DeCesare et al. |
| 7,150,747 B1 | 12/2006 | McDonald et al. |
| 7,150,748 B2 | 12/2006 | Ebbutt et al. |
| 7,153,300 B2 | 12/2006 | Goble |
| 7,156,845 B2 | 1/2007 | Mulier et al. |
| 7,166,105 B2 | 1/2007 | Mulier et al. |
| 7,166,106 B2 | 1/2007 | Bartel et al. |
| 7,169,143 B2 | 1/2007 | Eggers et al. |
| 7,169,144 B2 | 1/2007 | Hoey et al. |
| 7,207,471 B2 | 4/2007 | Heinrich et al. |
| 7,232,440 B2 | 6/2007 | Dumbauld et al. |
| 7,247,155 B2 | 7/2007 | Hoey et al. |
| 7,261,711 B2 | 8/2007 | Mulier et al. |
| 7,309,325 B2 | 12/2007 | Mulier et al. |
| 7,311,708 B2 | 12/2007 | McClurken |
| 7,322,974 B2 | 1/2008 | Swoyer et al. |
| 7,361,175 B2 | 4/2008 | Suslov |
| 7,364,579 B2 | 4/2008 | Mulier et al. |
| 2001/0014819 A1 | 8/2001 | Ingle et al. |
| 2001/0020167 A1 | 9/2001 | Woloszko et al. |
| 2001/0023365 A1 | 9/2001 | Medhkour et al. |
| 2001/0025178 A1 | 9/2001 | Mulier et al. |
| 2001/0032002 A1 | 10/2001 | McClurken et al. |
| 2001/0039419 A1 | 11/2001 | Francischelli et al. |
| 2001/0041921 A1 | 11/2001 | Mulier et al. |
| 2001/0051802 A1 | 12/2001 | Woloszko et al. |
| 2001/0051804 A1 | 12/2001 | Mulier et al. |
| 2002/0002393 A1 | 1/2002 | Mitchell |
| 2002/0010463 A1 | 1/2002 | Mulier et al. |
| 2002/0013582 A1 | 1/2002 | Mulier et al. |
| 2002/0016589 A1 | 2/2002 | Swartz et al. |
| 2002/0019628 A1 | 2/2002 | Comben |
| 2002/0022870 A1 | 2/2002 | Truckai et al. |
| 2002/0026186 A1 | 2/2002 | Woloszko et al. |
| 2002/0026187 A1 | 2/2002 | Swanson |
| 2002/0029036 A1 | 3/2002 | Goble et al. |
| 2002/0035361 A1 | 3/2002 | Houser et al. |
| 2002/0035387 A1 | 3/2002 | Mulier et al. |
| 2002/0049438 A1 | 4/2002 | Sharkey et al. |
| 2002/0049439 A1 | 4/2002 | Mulier et al. |
| 2002/0049483 A1 | 4/2002 | Knowlton |
| 2002/0058933 A1 | 5/2002 | Christopherson et al. |
| 2002/0058935 A1 | 5/2002 | Hoey et al. |
| 2002/0062123 A1 | 5/2002 | McClurken et al. |
| 2002/0095150 A1 | 7/2002 | Goble |
| 2002/0095151 A1 | 7/2002 | Dahla et al. |
| 2002/0095152 A1 | 7/2002 | Ciarrocca et al. |
| 2002/0099366 A1 | 7/2002 | Dahla et al. |
| 2002/0115991 A1 | 8/2002 | Edwards |
| 2002/0115992 A1 | 8/2002 | Utley et al. |
| 2002/0120259 A1 | 8/2002 | Lettice et al. |
| 2002/0120260 A1 | 8/2002 | Morris et al. |
| 2002/0120261 A1 | 8/2002 | Morris et al. |
| 2002/0128650 A1 | 9/2002 | McClurken |
| 2002/0133148 A1 | 9/2002 | Daniel et al. |
| 2002/0151884 A1 | 10/2002 | Hoey et al. |

| | | | | | | |
|---|---|---|---|---|---|---|
| 2002/0156511 A1 | 10/2002 | Habib | | 2004/0143263 A1* | 7/2004 | Schechter et al. ............... 606/51 |
| 2002/0161364 A1 | 10/2002 | Mulier et al. | | 2004/0147902 A1 | 7/2004 | McGuckin, Jr. et al. |
| 2002/0169446 A1 | 11/2002 | Mulier et al. | | 2004/0147916 A1 | 7/2004 | Baker |
| 2002/0177846 A1 | 11/2002 | Mulier et al. | | 2004/0147922 A1 | 7/2004 | Keppel |
| 2002/0183733 A1 | 12/2002 | Mulier et al. | | 2004/0147925 A1 | 7/2004 | Buysse et al. |
| 2002/0188284 A1 | 12/2002 | To et al. | | 2004/0162552 A1 | 8/2004 | McClurken |
| 2002/0193851 A1 | 12/2002 | Silverman et al. | | 2004/0162554 A1 | 8/2004 | Lee et al. |
| 2002/0198524 A1 | 12/2002 | Mulier et al. | | 2004/0162557 A1 | 8/2004 | Tetzlaff et al. |
| 2003/0004510 A1 | 1/2003 | Wham et al. | | 2004/0162572 A1 | 8/2004 | Sauer |
| 2003/0014050 A1 | 1/2003 | Sharkey et al. | | 2004/0167508 A1 | 8/2004 | Wham et al. |
| 2003/0032954 A1 | 2/2003 | Carranza et al. | | 2004/0172111 A1 | 9/2004 | Hijii et al. |
| 2003/0032955 A1 | 2/2003 | Mulier et al. | | 2004/0176760 A1 | 9/2004 | Qiu |
| 2003/0073989 A1 | 4/2003 | Hoey et al. | | 2004/0176761 A1 | 9/2004 | Desinger |
| 2003/0073993 A1 | 4/2003 | Ciarrocca | | 2004/0176762 A1 | 9/2004 | Lawes et al. |
| 2003/0114850 A1 | 6/2003 | McClurken et al. | | 2004/0181219 A1 | 9/2004 | Goble et al. |
| 2003/0181902 A1 | 9/2003 | Mulier et al. | | 2004/0181250 A1 | 9/2004 | Adams et al. |
| 2003/0204185 A1 | 10/2003 | Sherman et al. | | 2004/0186469 A1 | 9/2004 | Woloszko et al. |
| 2003/0216733 A1 | 11/2003 | McClurken et al. | | 2004/0186470 A1 | 9/2004 | Goble et al. |
| 2004/0015162 A1 | 1/2004 | McGaffigan | | 2004/0186535 A1 | 9/2004 | Knowlton |
| 2004/0015163 A1 | 1/2004 | Buysse et al. | | 2004/0193148 A1 | 9/2004 | Wham et al. |
| 2004/0015215 A1 | 1/2004 | Fredricks et al. | | 2004/0193150 A1 | 9/2004 | Sharkey et al. |
| 2004/0015216 A1 | 1/2004 | DeSisto | | 2004/0193152 A1 | 9/2004 | Sutton et al. |
| 2004/0015218 A1 | 1/2004 | Finch et al. | | 2004/0193211 A1 | 9/2004 | Voegele et al. |
| 2004/0019350 A1 | 1/2004 | O'Brien et al. | | 2004/0199156 A1 | 10/2004 | Rioux et al. |
| 2004/0024395 A1 | 2/2004 | Ellman et al. | | 2004/0199160 A1 | 10/2004 | Slater |
| 2004/0024396 A1 | 2/2004 | Eggers | | 2004/0206365 A1 | 10/2004 | Knowlton |
| 2004/0024398 A1 | 2/2004 | Hovda et al. | | 2004/0210213 A1 | 10/2004 | Fuimaono et al. |
| 2004/0024399 A1 | 2/2004 | Sharps et al. | | 2004/0210214 A1 | 10/2004 | Knowlton |
| 2004/0030327 A1 | 2/2004 | Golan | | 2004/0215181 A1 | 10/2004 | Christopherson et al. |
| 2004/0030328 A1 | 2/2004 | Eggers et al. | | 2004/0215182 A1 | 10/2004 | Lee |
| 2004/0030330 A1 | 2/2004 | Brassell et al. | | 2004/0215183 A1 | 10/2004 | Hoey et al. |
| 2004/0030332 A1 | 2/2004 | Knowlton et al. | | 2004/0215184 A1 | 10/2004 | Eggers et al. |
| 2004/0030333 A1 | 2/2004 | Goble | | 2004/0215185 A1 | 10/2004 | Truckai et al. |
| 2004/0034340 A1 | 2/2004 | Biscup | | 2004/0215188 A1 | 10/2004 | Mulier et al. |
| 2004/0034346 A1 | 2/2004 | Stern et al. | | 2004/0215235 A1 | 10/2004 | Jackson et al. |
| 2004/0034349 A1 | 2/2004 | Kirwan, Jr. et al. | | 2004/0215296 A1 | 10/2004 | Ganz et al. |
| 2004/0034400 A1 | 2/2004 | Ingle et al. | | 2004/0220561 A1 | 11/2004 | Kirwan, Jr. et al. |
| 2004/0039429 A1 | 2/2004 | Daniel et al. | | 2004/0220562 A1 | 11/2004 | Garabedian et al. |
| 2004/0044341 A1 | 3/2004 | Truckai et al. | | 2004/0225288 A1 | 11/2004 | Buysse et al. |
| 2004/0054363 A1 | 3/2004 | Vaska et al. | | 2004/0230190 A1 | 11/2004 | Dahla et al. |
| 2004/0054365 A1 | 3/2004 | Goble | | 2004/0236322 A1 | 11/2004 | Mulier et al. |
| 2004/0054366 A1 | 3/2004 | Davison et al. | | 2004/0236324 A1 | 11/2004 | Muller et al. |
| 2004/0054369 A1 | 3/2004 | Nelson et al. | | 2004/0243125 A1 | 12/2004 | Dycus et al. |
| 2004/0054370 A1 | 3/2004 | Given | | 2004/0243163 A1 | 12/2004 | Casiano et al. |
| 2004/0059328 A1 | 3/2004 | Daniel et al. | | 2004/0249371 A1 | 12/2004 | Dycus et al. |
| 2004/0059363 A1 | 3/2004 | Alvarez et al. | | 2004/0249374 A1 | 12/2004 | Tetzlaff et al. |
| 2004/0064023 A1 | 4/2004 | Ryan et al. | | 2004/0249425 A1 | 12/2004 | Roy et al. |
| 2004/0064137 A1 | 4/2004 | Pellegrino et al. | | 2004/0260279 A1 | 12/2004 | Goble et al. |
| 2004/0068306 A1 | 4/2004 | Shadduck | | 2004/0260280 A1 | 12/2004 | Sartor |
| 2004/0068307 A1 | 4/2004 | Goble | | 2004/0260368 A1 | 12/2004 | Ingle et al. |
| 2004/0073205 A1 | 4/2004 | Treat et al. | | 2005/0010205 A1 | 1/2005 | Hovda et al. |
| 2004/0073208 A1 | 4/2004 | Sutter | | 2005/0010212 A1 | 1/2005 | McClurken et al. |
| 2004/0078034 A1 | 4/2004 | Acker et al. | | 2005/0015085 A1 | 1/2005 | McClurken et al. |
| 2004/0078037 A1 | 4/2004 | Batchelor et al. | | 2005/0015086 A1 | 1/2005 | Platt |
| 2004/0078038 A1 | 4/2004 | Desinger et al. | | 2005/0015130 A1 | 1/2005 | Gill |
| 2004/0082946 A1 | 4/2004 | Malis et al. | | 2005/0021025 A1 | 1/2005 | Buysse et al. |
| 2004/0082952 A1 | 4/2004 | Dycus et al. | | 2005/0021026 A1 | 1/2005 | Baily |
| 2004/0087937 A1 | 5/2004 | Eggers et al. | | 2005/0021027 A1 | 1/2005 | Shields et al. |
| 2004/0087939 A1 | 5/2004 | Eggers et al. | | 2005/0033278 A1 | 2/2005 | McClurken et al. |
| 2004/0087940 A1 | 5/2004 | Jahns et al. | | 2005/0033292 A1 | 2/2005 | Teitelbaum et al. |
| 2004/0087943 A1 | 5/2004 | Dycus et al. | | 2005/0038471 A1 | 2/2005 | Chan et al. |
| 2004/0088029 A1 | 5/2004 | Yamamoto | | 2005/0043728 A1 | 2/2005 | Ciarrocca |
| 2004/0092925 A1 | 5/2004 | Rizoiu et al. | | 2005/0049583 A1 | 3/2005 | Swanson |
| 2004/0092926 A1 | 5/2004 | Hoey et al. | | 2005/0049586 A1 | 3/2005 | Daniel et al. |
| 2004/0097919 A1 | 5/2004 | Wellman et al. | | 2005/0055019 A1 | 3/2005 | Skarda |
| 2004/0102770 A1 | 5/2004 | Goble | | 2005/0055020 A1 | 3/2005 | Skarda |
| 2004/0102824 A1 | 5/2004 | Sharkey et al. | | 2005/0059966 A1 | 3/2005 | McClurken et al. |
| 2004/0111136 A1 | 6/2004 | Sharkey et al. | | 2005/0070888 A1 | 3/2005 | Dimatteo et al. |
| 2004/0111137 A1 | 6/2004 | Sharkey et al. | | 2005/0070891 A1 | 3/2005 | DeSisto |
| 2004/0116923 A1 | 6/2004 | Desinger | | 2005/0070894 A1 | 3/2005 | McClurken |
| 2004/0122420 A1 | 6/2004 | Amoah | | 2005/0070896 A1 | 3/2005 | Daniel et al. |
| 2004/0122423 A1 | 6/2004 | Dycus et al. | | 2005/0080410 A1 | 4/2005 | Rioux et al. |
| 2004/0122494 A1 | 6/2004 | Eggers et al. | | 2005/0080413 A1 | 4/2005 | Canady |
| 2004/0138654 A1 | 7/2004 | Goble | | 2005/0085804 A1 | 4/2005 | McGaffigan |
| 2004/0138655 A1 | 7/2004 | McClurken et al. | | 2005/0085809 A1 | 4/2005 | Mucko et al. |
| 2004/0138657 A1 | 7/2004 | Bourne et al. | | 2005/0085880 A1 | 4/2005 | Truckai et al. |
| 2004/0143257 A1 | 7/2004 | Fuimaono | | 2005/0090816 A1 | 4/2005 | McClurken et al. |
| 2004/0143258 A1 | 7/2004 | Fuimaono | | 2005/0090819 A1 | 4/2005 | Goble |
| 2004/0143259 A1 | 7/2004 | Mulier et al. | | 2005/0096649 A1 | 5/2005 | Adams |

| | | |
|---|---|---|
| 2005/0096651 A1 | 5/2005 | Truckai et al. |
| 2005/0101951 A1 | 5/2005 | Wham et al. |
| 2005/0101952 A1 | 5/2005 | Lands et al. |
| 2005/0101965 A1 | 5/2005 | Ryan |
| 2005/0107778 A1 | 5/2005 | Rioux et al. |
| 2005/0107779 A1 | 5/2005 | Ellman et al. |
| 2005/0107784 A1 | 5/2005 | Moses et al. |
| 2005/0107786 A1 | 5/2005 | Canady |
| 2005/0113820 A1 | 5/2005 | Goble et al. |
| 2005/0113825 A1 | 5/2005 | Cosmescu |
| 2005/0124987 A1 | 6/2005 | Goble |
| 2005/0130929 A1 | 6/2005 | Boyd |
| 2005/0131402 A1 | 6/2005 | Ciarrocca et al. |
| 2005/0137590 A1 | 6/2005 | Lawes et al. |
| 2005/0137662 A1 | 6/2005 | Morris et al. |
| 2005/0143729 A1 | 6/2005 | Francischelli et al. |
| 2005/0154385 A1 | 7/2005 | Heim et al. |
| 2005/0154433 A1 | 7/2005 | Levy, Jr. et al. |
| 2005/0159739 A1 | 7/2005 | Paul et al. |
| 2005/0159740 A1 | 7/2005 | Paul et al. |
| 2005/0159778 A1 | 7/2005 | Heinrich et al. |
| 2005/0159797 A1 | 7/2005 | Chandran et al. |
| 2005/0165444 A1 | 7/2005 | Hart et al. |
| 2005/0171524 A1 | 8/2005 | Stern et al. |
| 2005/0171526 A1 | 8/2005 | Rioux et al. |
| 2005/0171532 A1 | 8/2005 | Ciarrocca |
| 2005/0171533 A1 | 8/2005 | Latterell et al. |
| 2005/0171534 A1 | 8/2005 | Habib |
| 2005/0171583 A1 | 8/2005 | Mosher et al. |
| 2005/0177150 A1 | 8/2005 | Amoah et al. |
| 2005/0177209 A1 | 8/2005 | Leung et al. |
| 2005/0187543 A1 | 8/2005 | Underwood et al. |
| 2005/0187599 A1 | 8/2005 | Sharkey et al. |
| 2005/0203503 A1 | 9/2005 | Edwards et al. |
| 2005/0203504 A1 | 9/2005 | Wham et al. |
| 2005/0209591 A1 | 9/2005 | Sutter |
| 2005/0209621 A1 | 9/2005 | Gordon et al. |
| 2005/0222602 A1 | 10/2005 | Sutter et al. |
| 2005/0222611 A1 | 10/2005 | WeitKamp |
| 2005/0228372 A1 | 10/2005 | Truckai et al. |
| 2005/0245918 A1 | 11/2005 | Sliwa, Jr. et al. |
| 2005/0245921 A1 | 11/2005 | Strul et al. |
| 2005/0245922 A1 | 11/2005 | Goble |
| 2005/0245923 A1 | 11/2005 | Christopherson et al. |
| 2005/0250477 A1 | 11/2005 | Eastwood et al. |
| 2005/0251128 A1 | 11/2005 | Amoah |
| 2005/0251134 A1 | 11/2005 | Woloszko et al. |
| 2005/0256519 A1 | 11/2005 | Goble et al. |
| 2005/0261676 A1 | 11/2005 | Hall et al. |
| 2005/0261677 A1 | 11/2005 | Hall et al. |
| 2005/0267465 A1 | 12/2005 | Hillier et al. |
| 2005/0267467 A1 | 12/2005 | Paul et al. |
| 2005/0267468 A1 | 12/2005 | Truckai et al. |
| 2005/0267469 A1 | 12/2005 | Blocher |
| 2005/0273092 A1 | 12/2005 | G. et al. |
| 2005/0273097 A1 | 12/2005 | Ryan |
| 2005/0277915 A1 | 12/2005 | DeCesare et al. |
| 2005/0277916 A1 | 12/2005 | DeCesare et al. |
| 2005/0277917 A1 | 12/2005 | Garito et al. |
| 2005/0283147 A1 | 12/2005 | Yachi |
| 2005/0283148 A1 | 12/2005 | Janssen et al. |
| 2005/0283149 A1 | 12/2005 | Thorne et al. |
| 2005/0283150 A1 | 12/2005 | Moutafis et al. |
| 2005/0283151 A1 | 12/2005 | Ebbutt et al. |
| 2005/0288661 A1 | 12/2005 | Sauvageau et al. |
| 2005/0288665 A1 | 12/2005 | Woloszko |
| 2006/0004356 A1 | 1/2006 | Bilski et al. |
| 2006/0009760 A1 | 1/2006 | Mulier et al. |
| 2006/0009762 A1 | 1/2006 | Whayne |
| 2006/0015097 A1 | 1/2006 | Mulier et al. |
| 2006/0020265 A1 | 1/2006 | Ryan |
| 2006/0025765 A1 | 2/2006 | Landman et al. |
| 2006/0025766 A1 | 2/2006 | Heinrich et al. |
| 2006/0030912 A1 | 2/2006 | Eggers et al. |
| 2006/0036235 A1 | 2/2006 | Swoyer et al. |
| 2006/0036237 A1 | 2/2006 | Davison et al. |
| 2006/0036239 A1 | 2/2006 | Canady |
| 2006/0041254 A1 | 2/2006 | Francischelli et al. |
| 2006/0041255 A1 | 2/2006 | Eggers et al. |
| 2006/0047275 A1 | 3/2006 | Goble |
| 2006/0047280 A1 | 3/2006 | Goble et al. |
| 2006/0047331 A1 | 3/2006 | Lax et al. |
| 2006/0052770 A1 | 3/2006 | Mulier et al. |
| 2006/0064085 A1 | 3/2006 | Schechter et al. |
| 2006/0064101 A1 | 3/2006 | Arramon |
| 2006/0074411 A1 | 4/2006 | Carmel et al. |
| 2006/0074414 A1 | 4/2006 | Mulier et al. |
| 2006/0079872 A1 | 4/2006 | Eggleston |
| 2006/0079888 A1 | 4/2006 | Mulier et al. |
| 2006/0084968 A1 | 4/2006 | Truckai et al. |
| 2006/0095026 A1 | 5/2006 | Ricart et al. |
| 2006/0095031 A1 | 5/2006 | Ormsby |
| 2006/0095034 A1 | 5/2006 | Garito et al. |
| 2006/0095075 A1 | 5/2006 | Burkinshaw et al. |
| 2006/0095103 A1 | 5/2006 | Eggers et al. |
| 2006/0100619 A1 | 5/2006 | McClurken et al. |
| 2006/0106376 A1 | 5/2006 | Godara et al. |
| 2006/0106379 A1 | 5/2006 | O'Brien et al. |
| 2006/0111705 A1 | 5/2006 | Janzen et al. |
| 2006/0111709 A1 | 5/2006 | Goble et al. |
| 2006/0111710 A1 | 5/2006 | Goble et al. |
| 2006/0111711 A1 | 5/2006 | Goble |
| 2006/0111741 A1 | 5/2006 | Nardella |
| 2006/0116675 A1 | 6/2006 | McClurken et al. |
| 2006/0122593 A1 | 6/2006 | Jun et al. |
| 2006/0129145 A1 | 6/2006 | Woloszko et al. |
| 2006/0129185 A1 | 6/2006 | Paternuosto |
| 2006/0142757 A1 | 6/2006 | Daniel et al. |
| 2006/0149225 A1 | 7/2006 | McClurken |
| 2006/0167446 A1 | 7/2006 | Pozzato |
| 2006/0167449 A1 | 7/2006 | Mulier et al. |
| 2006/0167451 A1 | 7/2006 | Cropper |
| 2006/0178667 A1 | 8/2006 | Sartor et al. |
| 2006/0178668 A1 | 8/2006 | Albritton, IV |
| 2006/0178670 A1 | 8/2006 | Woloszko et al. |
| 2006/0178699 A1 | 8/2006 | Surti |
| 2006/0184164 A1 | 8/2006 | Malis et al. |
| 2006/0184167 A1 | 8/2006 | Vaska et al. |
| 2006/0189977 A1 | 8/2006 | Allen et al. |
| 2006/0189979 A1 | 8/2006 | Esch et al. |
| 2006/0195079 A1 | 8/2006 | Eberl |
| 2006/0200123 A1 | 9/2006 | Ryan |
| 2006/0217700 A1 | 9/2006 | Garito et al. |
| 2006/0217701 A1 | 9/2006 | Young et al. |
| 2006/0217707 A1 | 9/2006 | Daniel et al. |
| 2006/0224154 A1 | 10/2006 | Shadduck et al. |
| 2006/0235286 A1 | 10/2006 | Stone et al. |
| 2006/0235377 A1 | 10/2006 | Earley et al. |
| 2006/0235379 A1 | 10/2006 | McClurken et al. |
| 2006/0241577 A1 | 10/2006 | Balbierz et al. |
| 2006/0241587 A1 | 10/2006 | Heim et al. |
| 2006/0241588 A1 | 10/2006 | Heim et al. |
| 2006/0241589 A1 | 10/2006 | Heim et al. |
| 2006/0247614 A1 | 11/2006 | Sampson et al. |
| 2006/0259025 A1 | 11/2006 | Dahla |
| 2006/0259031 A1 | 11/2006 | Carmel et al. |
| 2006/0259070 A1 | 11/2006 | Livneh |
| 2006/0264927 A1 | 11/2006 | Ryan |
| 2006/0264929 A1 | 11/2006 | Goble et al. |
| 2006/0264931 A1 | 11/2006 | Chapman et al. |
| 2006/0271033 A1 | 11/2006 | Ein-Gal |
| 2006/0271036 A1 | 11/2006 | Garabedian et al. |
| 2006/0271042 A1 | 11/2006 | Latterell et al. |
| 2006/0276783 A1 | 12/2006 | Cosmescu |
| 2006/0276785 A1 | 12/2006 | Asahara et al. |
| 2007/0000501 A1 | 1/2007 | Wert et al. |
| 2007/0010812 A1 | 1/2007 | Mittelstein et al. |
| 2007/0016182 A1 | 1/2007 | Lipson et al. |
| 2007/0049920 A1 | 3/2007 | McClurken et al. |
| 2007/0093808 A1 | 4/2007 | Mulier et al. |
| 2007/0118114 A1 | 5/2007 | Mulier et al. |
| 2007/0208332 A1 | 9/2007 | Mulier et al. |
| 2008/0015563 A1 | 1/2008 | Hoey et al. |
| 2008/0071270 A1 | 3/2008 | Desinger et al. |

FOREIGN PATENT DOCUMENTS

| | | |
|---|---|---|
| JP | 5-092009 A | 4/1993 |
| JP | 7-124245 A | 5/1995 |

| | | |
|---|---|---|
| WO | WO 97/05829 A1 | 2/1997 |
| WO | WO 98/38932 A1 | 9/1998 |
| WO | WO 99/66850 A1 | 12/1999 |
| WO | WO 00/62727 A1 | 10/2000 |
| WO | WO 00/78240 A1 | 12/2000 |
| WO | WO 01/28444 A1 | 4/2001 |
| WO | WO 01/80757 A2 | 11/2001 |
| WO | WO 2005/122938 A1 | 12/2005 |
| WO | WO 2006/062916 A2 | 6/2006 |
| WO | WO 2006/062939 A2 | 6/2006 |

OTHER PUBLICATIONS

English language abstract for JP 5-092009 A, published Apr. 16, 1993, 1 page.

English language abstract for JP 7-124245 A, published May 16, 1995, 1 page.

Finger, P.T. et al., "Heat Shrinkage of Extraocular Muscle Tendon", *Arch. Ophthalmol.*, vol. 105, No. 5, pp. 716-718 (May 1987).

Selecky, M.T. et al., "The Effects of Laser-Induced Collagen Shortening on the Biomechanical Properties of the Inferior Glenohumeral Ligament Complex," *Am. J. Sports Med.*, vol. 27, No. 2, pp. 168-172 (Mar./Apr. 1999).

Vangsness Jr., C.T. et al., "Collagen Shortening," *Clinical Orthopaedics and Related Research*, No. 337, pp. 267-271 (1997).

Wall, M.S. et al., "Thermal modification of collagen," *Journal of Shoulder and Elbow Surgery*, vol. 8, No. 4, pp. 339-344 (Jul./Aug. 1999).

\* cited by examiner

ELECTROSURGICAL DEVICE HAVING A TISSUE REDUCTION SENSOR

This application is a continuation of application Ser. No. 09/802,288, filed Mar. 8, 2001, now U.S. Pat. No. 6,689,131, which is incorporated herein by reference to the extent it is consistent.

TECHNICAL FIELD

The present invention relates generally to electrosurgical devices for use in surgical procedures and, more particularly, to an electrosurgical device having a sensor for detecting a change in tissue dimension.

BACKGROUND

Electrosurgical devices use electrical energy, most commonly radiofrequency ("RF") energy, to cut tissue and/or cauterize blood vessels. During use, a voltage gradient is created at the tip of the device, thereby, inducing current flow and related thermal energy generation in the tissue. With appropriate levels of electrical energy, the thermal energy generated is sufficient to cut or shrink the tissue being treated, or cauterize blood vessels.

Existing electrosurgical devices can cause the temperature of the tissue being treated (e.g., the tissue treatment zone) to rise significantly higher than 100 degrees C., resulting in tissue desiccation, tissue sticking to the electrodes, tissue perforation, char formation and/or smoke generation. Peak tissue temperatures as a result of RF treatment can be as high as 350 degrees C., and such high temperatures may be transmitted to adjacent tissue via thermal diffusion. Undesirable results of such transmission to adjacent tissue include unintended thermal damage to the tissue. To reduce these undesirable results, electrosurgical devices have been developed that simultaneously introduce a fluid (e.g., an electrolytic solution with RF applications) to the tissue treatment zone, thereby, distributing the thermal energy at the tissue treatment zone, and providing cooling as well.

In many applications, it is often desirable to allow the surgeon or operator of the electrosurgical device to control the dimensional changes of the tissue being treated. Typically, this is accomplished by monitoring the temperature at or near the tissue treatment zone. With some electrosurgical devices, the surgeon or operator can manually control the thermal energy being introduced to the tissue treatment zone. Alternatively, other electrosurgical devices can be configured to operate with a feedback control system to automatically control the thermal energy introduced to the tissue being treated. In either case, shortcomings with existing electrosurgical devices limit their effectiveness in controlling the dimensional changes of the tissue being treated.

In particular, existing electrosurgical devices monitor the temperature at or near the tissue treatment zone using a temperature sensor, such as, a thermocouple, thermistor, phosphor-coated optical fibers, or some other temperature sensor. Various factors often influence the temperature read by the temperature sensor including the temperature of the tissue being treated as well as any fluid being simultaneously infused at the tissue treatment zone. Furthermore, the temperature being read by the temperature sensor varies as the surgeon or operator moves the electrosurgical device into or out of the tissue treatment zone. As a result of these and other factors, it is often difficult to precisely achieve the desired dimensional change (e.g., the amount of shrinkage) of the tissue being treated.

Improvements in electrosurgical devices used in surgical procedures are, therefore, sought.

SUMMARY

In general terms, the present disclosure relates to an electrosurgical device for use in surgical procedures. More particularly, the present disclosure relates to an electrosurgical device having a sensor for detecting a change in tissue dimension, such as, tissue expansion or contraction. In one aspect, the electrosurgical device comprises a main body having a proximal end and a distal end. A heat delivery modality is situated and arranged at the distal end of the main body. A sensor arrangement is also situated and arranged at the distal end of the main body. The heat delivery modality provides thermal energy to a tissue being treated while the sensor arrangement is configured to engage and detect shrinkage of the tissue being treated. In one particular aspect, the heat delivery modality can be configured to provide a continuous flow of electrically conductive fluid to the tissue being treated while thermal energy is introduced.

Further in this aspect, the sensor arrangement can comprise at least one contact sensor situated and arranged at the distal end of the main body. In this aspect, the at least one contact sensor is constructed and arranged to engage and detect the shrinkage of the tissue being treated. Alternatively, the sensor arrangement can comprise first and second clamping members that are situated astride the main body. In this aspect, the first clamping member can include a first end pivotably connected at the main body and a second end opposite the first end. Similarly, the second clamping member can include a first end pivotably connected at the main body and a second end opposite the first end. Each of the second ends of the first and second clamping members can be constructed and arranged to engage and detect shrinkage of the tissue being treated such that the first and second clamping members rotate inwardly with respect to one another.

Still further in this aspect, the first clamping member can include a first mechanical stop for limiting the rotation of the first clamping member. Similarly, the second clamping member can include a second mechanical stop for limiting the rotation of the second clamping member. Accordingly, the first and second mechanical stops can be configured to limit the rotation of the first and second clamping members when the tissue being treated achieves a pre-determined shrinkage level.

Still further in this aspect, the first clamping member can include a first jaw and a second jaw at the second end of the first clamping member. The first and second jaws of the first clamping member can be selectively adjustable to grasp the tissue being treated. Likewise, the second clamping member can include a first jaw and a second jaw at the second end of the second clamping member. The first and second jaws of the second clamping member can be selectively adjustable to grasp the tissue being treated. Furthermore, each of the first and second jaws of the first clamping member can include a textured inner surface for resistively contacting the tissue being treated. Each of the first and second jaws of the second clamping member can also include a textured inner surface for resistively contacting the tissue being treated. Additionally, each of the first and second jaws of the first clamping member can include a solution delivery channel for delivery of a conductive solution to the tissue being treated. Similarly, each of the first and second jaws of the second clamping member can include a solution delivery channel for delivery of a conductive solution to the tissue being treated.

The heat delivery modality can include a first electrode arrangement operable with the first clamping member. The first electrode arrangement can be coupled to a source of radio frequency energy. Similarly, the heat delivery modality can include a second electrode arrangement operable with the second clamping member. The second electrode arrangement can be coupled to the source of radio frequency energy. Moreover, the first electrode arrangement can include at least one wet electrode that is coupled to the source of radio frequency energy while the second electrode arrangement can include at least one wet electrode that is coupled to the source of radio frequency energy.

Further in this aspect, the electrosurgical device can include a forceps extending from the distal end of the main body between the first and second clamping members. The forceps can include a first arm and a second arm that is selectively adjustable to slidably receive the tissue being treated. In this aspect, the heat delivery modality can include a first electrode disposed at the first arm of the forceps and a second electrode disposed at the second arm of the forceps. Furthermore, both the first and second electrodes can be wet electrodes. Still further, the first arm of the forceps can include a first solution delivery channel for delivery of a conductive solution to the tissue being treated. Similarly, the second arm of the forceps can include a second solution delivery channel for delivery of a conductive solution to the tissue being treated.

The sensor arrangement can be configured to provide input to the heat delivery modality such that the thermal energy being provided by the heat delivery modality is varied according to the shrinkage of the tissue being treated. Alternatively, the thermal energy provided by the heat delivery modality can be minimized when the tissue being treated achieves a predetermined shrinkage level. Furthermore, the sensor arrangement can be operably connected to a displacement measurement device for measuring the change in shrinkage of the tissue being treated, such as, a linear potentiometer, an optical sensor, a spring/force sensor, or other measurement device.

In yet another aspect, the disclosure relates to an electrosurgical device comprising a main body having a proximal end and a distal end, a heat delivery modality situated and arranged at the distal end of the main body, and a sensor arrangement situated and arranged at the distal end of the main body. In this aspect, the heat delivery modality is capable of providing thermal energy to a tissue being treated as well as a continuous flow of electrically conductive fluid to the tissue being treated while thermal energy is introduced. The sensor arrangement is configured to engage and detect shrinkage of the tissue being treated and can comprise first and second clamping members that are situated astride the main body. In this aspect, the first clamping member can include a first end pivotably connected at the main body and a second end opposite the first end. Similarly, the second clamping member can include a first end pivotably connected at the main body and a second end opposite the first end. Each of the second ends of the first and second clamping members are preferably constructed and arranged to engage and detect shrinkage of the tissue being treated such that the first and second clamping members rotate inwardly with respect to one another.

Still further in this aspect, the first clamping member can include a first jaw and a second jaw at the second end of the first clamping member. The first and second jaws of the first clamping member can be selectively adjustable to grasp the tissue being treated. Likewise, the second clamping member can include a first jaw and a second jaw at the second end of the second clamping member. The first and second jaws of the second clamping member can be selectively adjustable to grasp the tissue being treated. Furthermore, each of the first and second jaws of the first clamping member can include a textured inner surface for resistively contacting the tissue being treated. Each of the first and second jaws of the second clamping member can also include a textured inner surface for resistively contacting the tissue being treated. Additionally, each of the first and second jaws of the first clamping member can include a solution delivery channel for delivery of a conductive solution to the tissue being treated. Similarly, each of the first and second jaws of the second clamping member can include a solution delivery channel for delivery of a conductive solution to the tissue being treated.

Still further in this aspect, the heat delivery modality can include a first electrode arrangement operable with the first clamping member and coupled to a source of radio frequency energy. Similarly, the heat delivery modality can include a second electrode arrangement operable with the second clamping member and coupled to the source of radio frequency energy. The first electrode arrangement can include at least one wet electrode that is coupled to the source of radio frequency energy. Similarly, the second electrode arrangement can include at least one wet electrode that is coupled to the source of radio frequency energy.

Further in this aspect, the electrosurgical device can include a forceps extending from the distal end of the main body between the first and second clamping members. The forceps can include a first arm and a second arm that is selectively adjustable to slidably receive the tissue being treated. In this aspect, the heat delivery modality can include a first wet electrode disposed at the first arm of the forceps and coupled to a source of radio frequency energy. Similarly, the heat delivery modality can include a second wet electrode disposed at the second arm of the forceps and coupled to a source of radio frequency energy. Still further, the first arm of the forceps can include a first solution delivery channel for delivery of a conductive solution to the tissue being treated. Similarly, the second arm of the forceps can include a second solution delivery channel for delivery of a conductive solution to the tissue being treated.

The sensor arrangement can be configured to provide input to the heat delivery modality such that the thermal energy being provided by the heat delivery modality is varied according to the shrinkage of the tissue being treated. Alternatively, the thermal energy provided by the heat delivery modality can be minimized when the tissue being treated achieves a predetermined shrinkage level. Furthermore, the sensor arrangement can be operably connected to a displacement measurement device for measuring the change in shrinkage of the tissue being treated, such as, a linear potentiometer, an optical sensor, a spring/force sensor, or other measurement device.

BRIEF DESCRIPTION OF THE DRAWINGS

The invention may be more completely understood in consideration of the following detailed description of various embodiments of the invention in connection with the accompanying drawings, in which.

Figure 1:
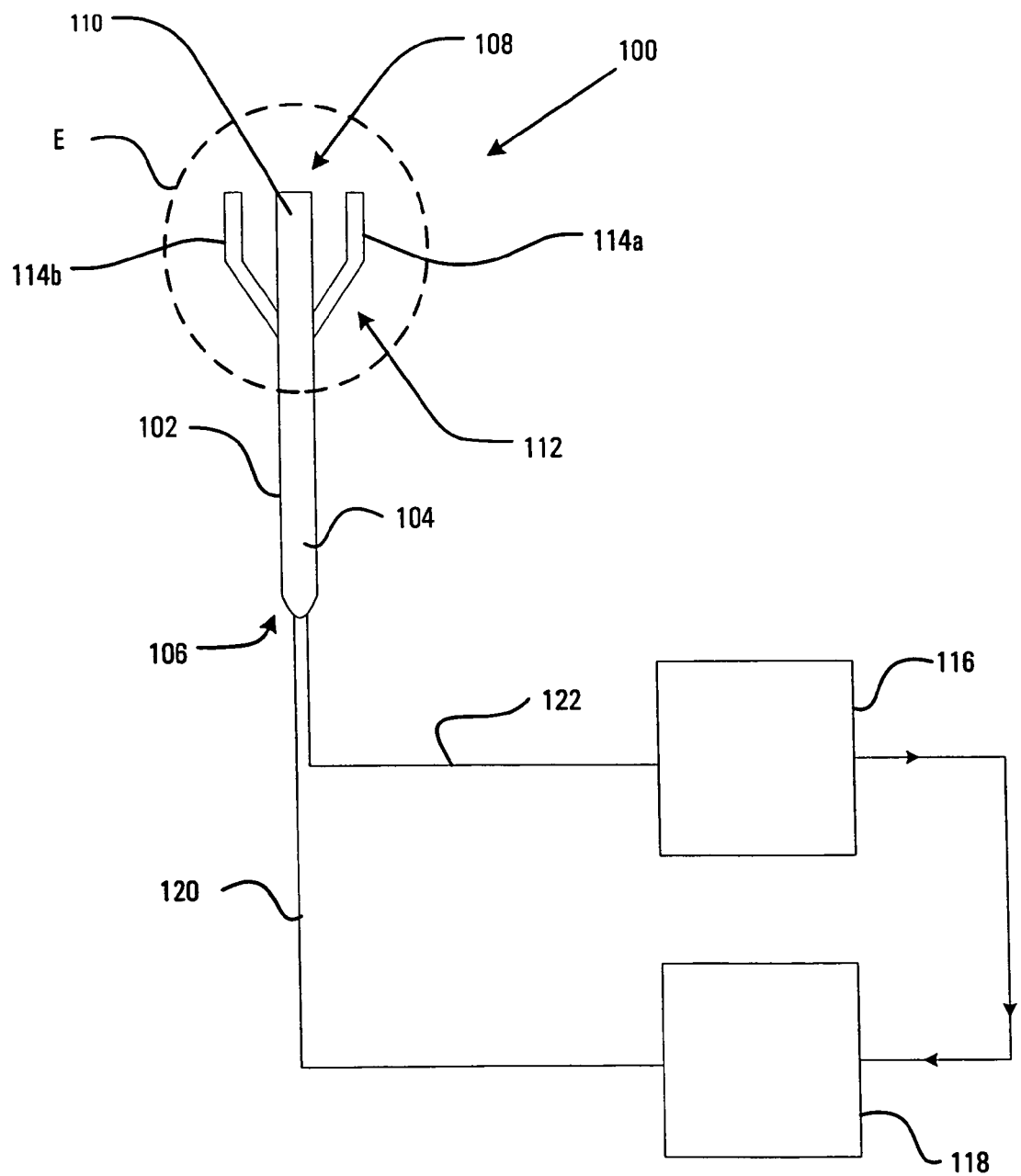
FIG. 1 is a high-level diagram illustrating one possible embodiment of an electrosurgical device having a sensor for detecting a change in tissue dimension in accordance with the present disclosure connected to a power source and an electronic controller.

While the invention is amenable to various modifications and alternative forms, specifics thereof have been shown by way of example in the drawings and will be described in detail. It should be understood, however, that the intention is not to limit the invention to the particular embodiments described. On the contrary, the intention is to cover all modifications, equivalents, and alternatives falling within the spirit and scope of the invention as defined by the appended claims.

DETAILED DESCRIPTION

Various embodiments of the present invention will be described in detail with reference to the drawings, wherein like reference numerals represent like parts and assemblies throughout the several views. Reference to various embodiments does not limit the scope of the present invention, which is limited only by the scope of the claims attached hereto.

The following discussion is intended to provide a brief, general description of a suitable medical device for precisely measuring and/or controlling a change in tissue dimension during surgical applications. As will become apparent from the discussion below in connection with the accompanying drawings, the present disclosure has particularized applicability to electrosurgical devices having a tissue reduction or shrinkage sensor. However, it will be appreciated by those having skill in the art that the present disclosure is not limited to the specific embodiments discussed below. Rather, the medical device of the present disclosure may be implemented during any surgical procedure where thermal energy is being used to contract and/or expand collagen and it is desirous to precisely measure and/or control the change in dimension of the tissue being treated. By "change in dimension," it is generally meant that the electrosurgical device of the present disclosure is able to measure and/or control the shortening, lengthening, widening, thinning, or other similar dimensional variations, of the tissue being treated.

Now referring to FIG. 1, a medical device or electrosurgical device 100 for use during surgical procedures in accordance with the principles of the present disclosure is shown. The electrosurgical device 100 generally includes a main body 102 having a proximal end 106 and a distal end 108. The phrase "proximal end" is generally meant to refer to the portion of the electrosurgical device 100 that is held in the operator's hand during use. Conversely, the phrase "distal end" is generally meant to refer to the portion of the electrosurgical device 100 at or near a location that contacts the patient. The main body 102 can include a handle portion 104 at or near its proximal end 106 and an end effector region E at or near its distal end 108. In the illustrated embodiment, the handle portion 104 depends downwardly along the main body portion 102 away from the end effector region E to provide a suitable area for gripping or handling the electrosurgical device 100 during use. By "downwardly," it is generally meant that in the orientation shown in FIG. 1, the handle portion 104 extends below the end effector region E.

As shown in FIG. 1, the electrosurgical device 100 is connected to a power source 118 via a pair of conductors 120. The power source 118 supplies energy to the electrosurgical device 100. Furthermore, as shown in the illustrated embodiment, the electrosurgical device 100 can be configured to provide feedback to an electronic controller 116 that is configured to modulate the energy supplied by the power source 118.

The end effector region E generally includes an arrangement for delivering thermal energy to the tissue (not shown) being treated. In the embodiments illustrated in the accompanying drawings, the arrangement for delivering thermal energy can comprise a heat delivery modality 110 capable heating the tissue being treated, thereby, causing the tissue to contract. However, as discussed above, one skilled in the art will readily appreciate that the arrangement for delivering thermal energy can comprise a device capable of cooling the tissue being treated, thereby, causing the tissue to expand. The heat delivery modality 110 generally can include any mechanism capable of delivering thermal energy to the tissue being treated, such as, RF energy, microwave energy, coherent (e.g., laser) and incoherent light energy, direct thermal transfer, electrical resistive heating, as well as other similar forms of energy. One skilled in the art will readily appreciate that the heat delivery modality 118 can be connected to any suitable energy source capable of introducing thermal energy to the tissue being treated, thereby, causing the tissue to contract.

In addition to the heat delivery modality 110, the end effector region E also includes a sensor arrangement 112. The sensor arrangement 112 generally can include any device capable of engaging and detecting a change in dimension, such as, shrinkage or expansion, of the tissue (not shown) being treated as thermal energy is introduced. For example, the sensor arrangement 112 can include at least one contact sensor situated and arranged at the distal end 108 of the main body 102. While many embodiments of the sensor arrangement 112 are contemplated, the sensor arrangement illustrated in FIG. 1, generally includes a first contact sensor 114a and a second contact sensor 114b, such as, clamping members, needles, or other devices, configured to grasp or embed within the tissue being treated. One or both of the contact sensors 114a, 114b can be pivotably attached to the main body 102 of the electrosurgical device 100 such that the contact sensors 114a, 114b move relative to the change in dimension of the tissue being treated. For example, in the illustrated embodiment, the contact sensors 114a, 114b move relative to the shrinkage of the tissue being treated. As a result, the sensor arrangement 112 is able to detect the shrinkage of the tissue being treated, thereby, allowing the surgeon or operator to precisely shrink or contract the tissue being treated.

For example, in one embodiment, the surgeon or operator can precisely shrink or contract the tissue by manually adjusting the power source 118 when the tissue shrinks to a desired level. Alternatively, as discussed above, the electrosurgical device 100 can be configured to provide a feedback control signal to the electronic controller 116 that is configured to modulate the energy supplied by the power source 118 such that the electrosurgical device 100 can automatically shrink or contract the tissue being treated to a predetermined level. The predetermined level can be established according to preset criteria, such as, shrinkage percentage or total tissue length reduction. Specific embodiments of the heat delivery modality 110 and the sensor arrangement 112 will be discussed in greater detail below.

Figure 2:
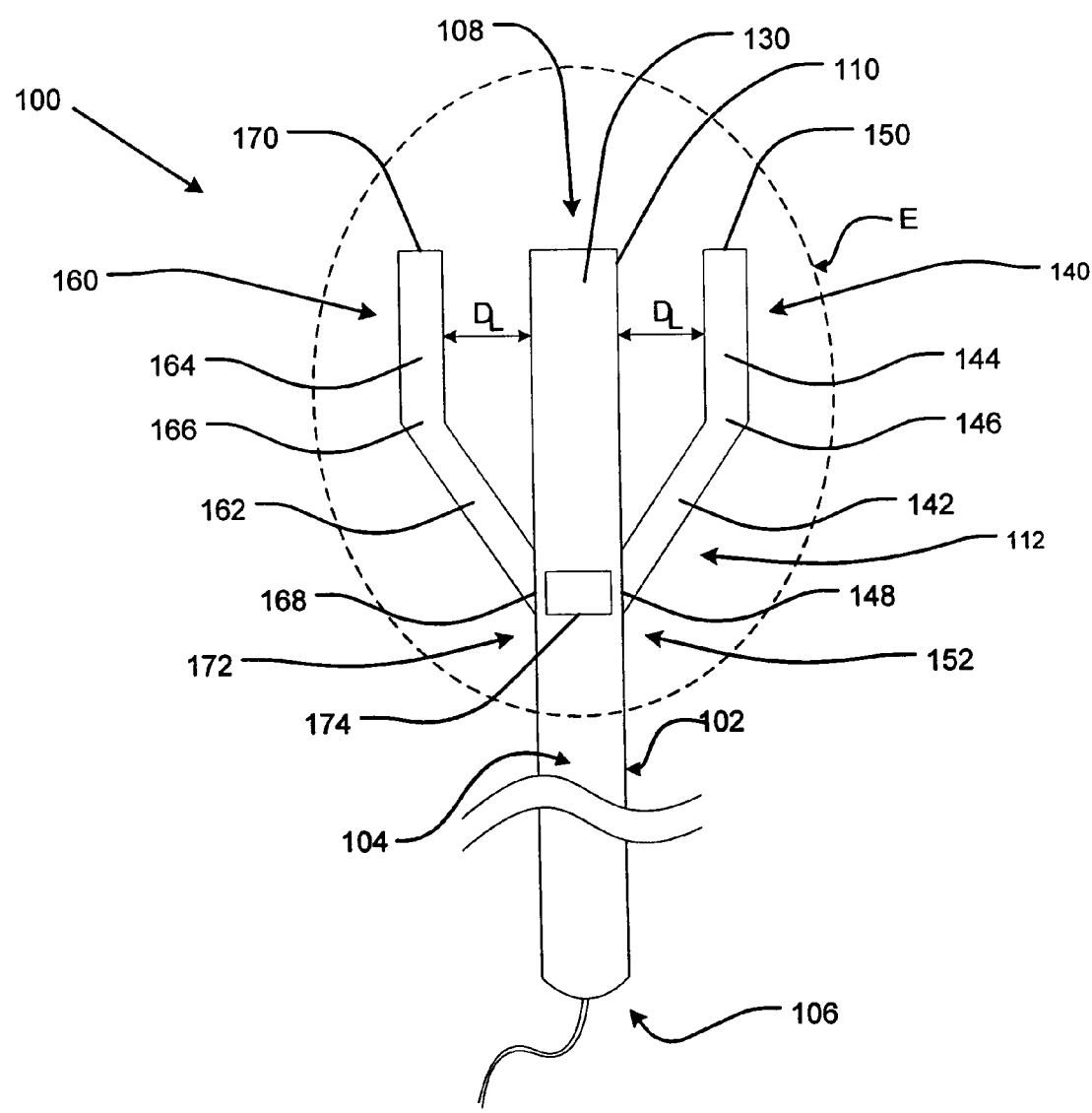
FIG. 2 is an enlarged, top view illustrating the electrosurgical device of FIG. 1 having a sensor for detecting a change in tissue dimension.
Figure 3:
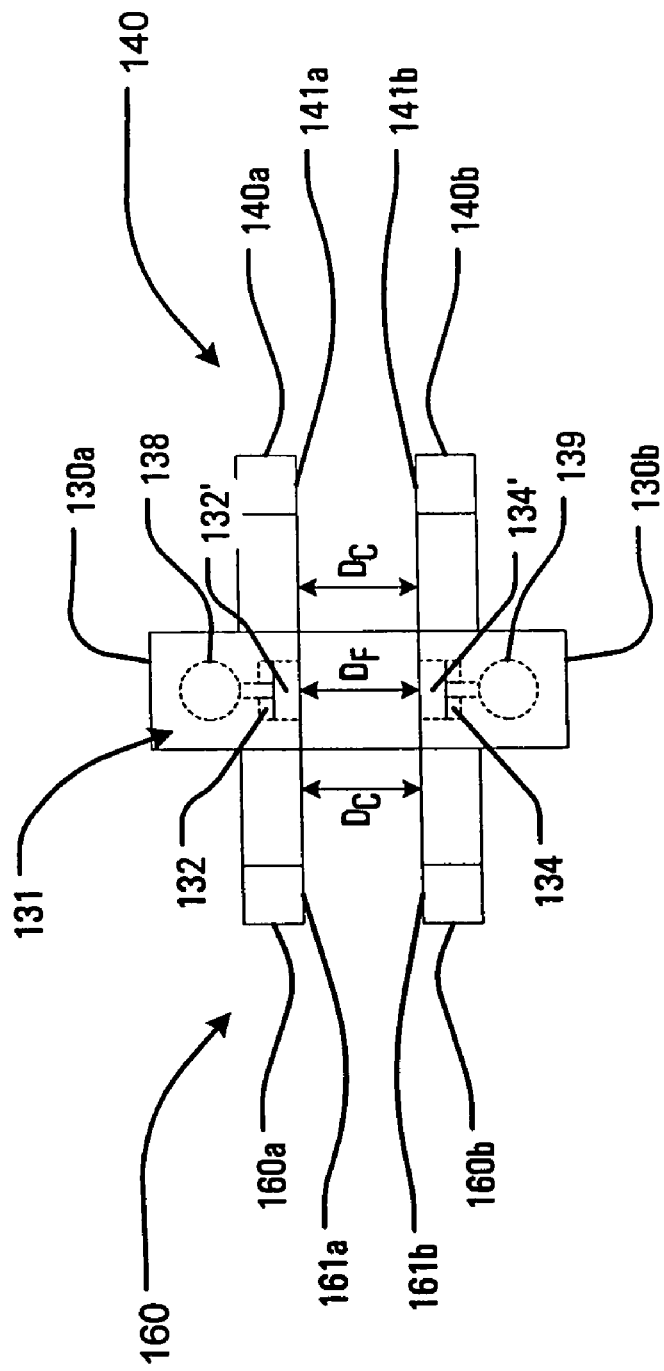
FIG. 3 is an enlarged, side section view illustrating the electrosurgical device of FIG. 2 having a sensor for detecting a change in tissue dimension.

A first embodiment of an electrosurgical device 100 for use in accordance with the principles of the present disclosure will now be described in connection with FIGS. 2-5. As shown in FIGS. 2 and 3, the end effector region E can include a forceps 130 for receiving the target tissue (not shown) to be treated. As shown in FIG. 3, the forceps 130 includes a first arm 130a and a second arm 130b. In the illustrated embodiment, the first and second arms 130a, 130b are spaced apart a distance $D_F$ to define a passageway therebetween. Preferably, the forceps 130 slidably receive the target tissue to be treated within the passageway defined between the first and second arms 130a, 130b. By "slidably receive," it is generally meant that the distance $D_F$ can be selectively adjusted such that the first and second arms 130a, 130b of the forceps 130 maintain slidable contact with and do not restrict the movement of the target tissue to be treated when it is received within the passageway. Thus, the forceps 130 allow the tissue being treated to shrink as thermal energy is introduced to the treatment zone.

The forceps 130 define a heat delivery modality 110 for providing thermal energy to the tissue (not shown) being treated. While many embodiments of the heat delivery modality 110 are contemplated, in the illustrated embodiment, the heat delivery modality 110 defined by the forceps 130 includes an electrode arrangement 131 for providing thermal energy to the tissue being treated. In particular, as shown in FIG. 3, the first arm 130a of the forceps 130 can include a first electrode 132, and the second arm 130b can include a second electrode 134 having a polarity opposite the first electrode 132. The electrode arrangement 131 illustrated in FIG. 3 is a bipolar configuration. However, one skilled in the art will readily appreciate that the electrosurgical device 100 of the present disclosure can be implemented using a monopolar electrode arrangement.

In one possible embodiment, the first and second electrodes 132, 134 can be selectively energized to provide thermal energy to the tissue being treated. In a preferred embodiment, the thermal energy supplied to the tissue being treated is produced as a result of a voltage gradient created by a RF energy power source 118 (FIG. 1). However, it will be appreciated that the thermal energy supplied to the tissue being treated can be provided by any suitable energy source sufficient to allow the tissue being treated to shrink or contract. For example, as discussed above, the energy source 118 connected to the heat delivery modality 131 can be microwave energy, coherent (e.g., laser) or incoherent light energy, direct thermal transfer, electrical resistive heating, as well as other similar forms or sources of energy.

Preferably, the electrode arrangement 131 discussed above is a wet electrode arrangement and is used in conjunction with a conductive fluid (e.g., an electrolytic solution). The use of a conductive fluid in connection with the electrode arrangement 131 allows the thermal energy to be distributed equally, thereby, minimizing hot spots within the tissue being treated. In the embodiment illustrated in FIG. 3, the first arm 130a of the forceps 130 (FIG. 2) is provided with a solution delivery channel 138. Similarly, the second arm 130b is provided with a solution delivery channel 139. The solution delivery channels 138, 139 provide a path for fluid communication between a fluid source (not shown) and the forceps 130. In particular, the solution delivery channel 138 provides a path for fluid communication between a fluid source and the first arm 130a and the solution delivery channel 139 provides a path for fluid communication between a fluid source and the second arm 130b. Fluid can flow from the solution delivery channel 138 through small holes (not shown) in the first electrode 132 and into a region 132' located between the first electrode 132 and the tissue (not shown). Similarly, fluid can flow from the solution delivery channel 139 through small holes (not shown) in the second electrode 134 and into a region 134' located between the second electrode 134 and the tissue. In so doing, the electrosurgical device 100 can introduce a conductive fluid, such as, a saline solution or other similar electrolytic solution, at the electrode/tissue interface to minimize the amount of tissue damage, char formation, smoke generation or other similar damage to the tissue being treated.

In addition to the heat delivery modality 110, the end effector region E also includes a sensor arrangement 112 configured to engage and detect a change in dimension of the tissue being treated. For example, in the illustrated embodiment, the sensor arrangement 112 can be used to measure the shrinkage or contraction of the tissue being treated. The sensor arrangement 112 generally includes at least one contact sensor situated and arranged at the distal end 108 of the main body 102. Exemplary contact sensors capable of engaging and detecting shrinkage of the tissue being treated include, but are not limited to, clamping members, needles, or other devices that can grasp or embed within the tissue being treated. While many embodiments of the sensor arrangement 112 are contemplated, in the illustrated embodiment, the sensor arrangement 112 includes a first clamp 140 and a second clamp 160 situated and arranged astride the forceps 130. By "astride," it is generally meant that the forceps 130 is situated and arranged between the first and second clamps 140, 160.

As shown in FIG. 3, the first clamp 140 can comprise first and second symmetrical jaw members 140a, 140b. Each of the jaw members 140a, 140b include a lower arm member 142 (FIG. 2) extending away from the main body portion 102 of the device 100 and an upper flange member 144 (FIG. 2). In this embodiment, an elbow or shoulder 146 (FIG. 2) is defined by the intersection of the lower arm member 142 and the upper flange 144. The first and second symmetrical jaw members 140a, 140b also include a proximal end portion 148 (FIG. 2) and a distal end portion 150 (FIG. 2). The phrase "proximal end portion" is generally meant to refer to the portion of each of the first and second jaw members 140a, 140b at or near their point of attachment to the main body 102. Likewise, the phrase "distal end portion" is generally meant to refer to the portion of each of the first and second jaw members 140a, 140b at or near a location furthest from their point of attachment to the main body 102.

Similarly, the second clamp 160 comprises first and second symmetrical jaw members 160a, 160b. Each of the jaw members 160a, 160b include a lower arm member 162 (FIG. 2) extending away from the main body portion 102 of the device 100 and an upper flange member 164 (FIG. 2). In this embodiment, an elbow or shoulder 166 (FIG. 2) is defined by the intersection of the lower arm member 162 and the upper flange 164. Each of the jaw members 160a, 160b comprising the second clamp 160 also include a proximal end portion 168 (FIG. 2) and a distal end portion 170 (FIG. 2). As with the first clamp 140 discussed above, the phrase "proximal end portion" is generally meant to refer to the portion of each of the first and second jaw members 160a, 160b at or near their point of attachment to the main body 102. Similarly, the phrase "distal end portion" is generally meant to refer to the portion of each of the jaw members 160a, 160b at or near a location furthest from their point of attachment to the main body 102.

In the illustrated embodiment, the first and second symmetrical jaw members 140a, 140b comprising the first clamp 140 are spaced apart a distance $D_c$ to define a passageway for receiving the tissue being treated. In one possible embodiment, the distance $D_c$ can be selectively adjusted, thereby, increasing or decreasing the compressive forces being applied to the tissue being treated. Moreover, the first and second jaw members 140a, 140b can include inner surfaces 141a, 141b, respectively, that resistively contact the tissue being treated. By "resistively contact," it is generally meant that the inner surfaces 141a, 141b are textured such that the first clamp 140 can maintain a grasp on the tissue being treated. For example, the inner surfaces 141a, 141b can include serrations, grooves, or any other surface roughness that increase the friction between the first clamp 140 and the tissue being treated.

Similarly, the first and second symmetrical jaw members 160a, 160b comprising the second clamp 160 are spaced apart a distance $D_c$ to define a passageway for receiving the tissue being treated. As discussed above in connection with the first clamp 140, in one possible embodiment, the distance $D_c$ can be selectively adjusted to increase or decrease the compressive forces being applied to the tissue being treated. Moreover, the first and second jaw members 160a, 160b comprising the second clamp 160 can include inner surfaces 161a, 161b that resistively contact the tissue being treated. By "resistively contact," it is generally meant that the inner surfaces 161a, 161b are textured such that the second clamp 160 maintains a grasp on the tissue being treated. For example, the inner surfaces 161a, 161b can include serrations, grooves, or any other similar surface roughness that increase the friction between the second clamp 160 and the tissue being treated.

Figure 4:
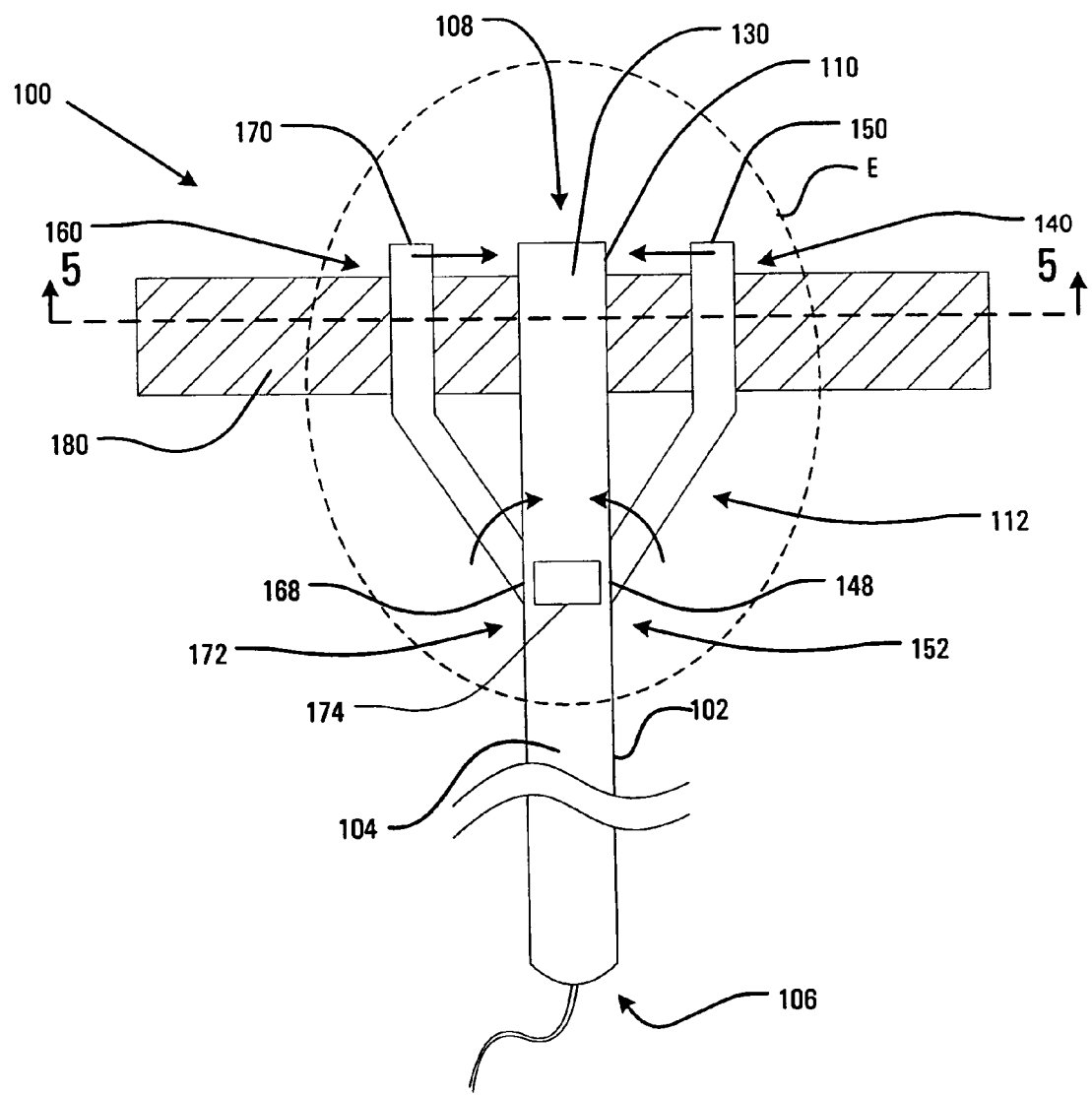
FIG. 4 is an enlarged, a top view illustrating the electrosurgical device of FIG. 2 having a tissue positioned within the device.
Figure 5:
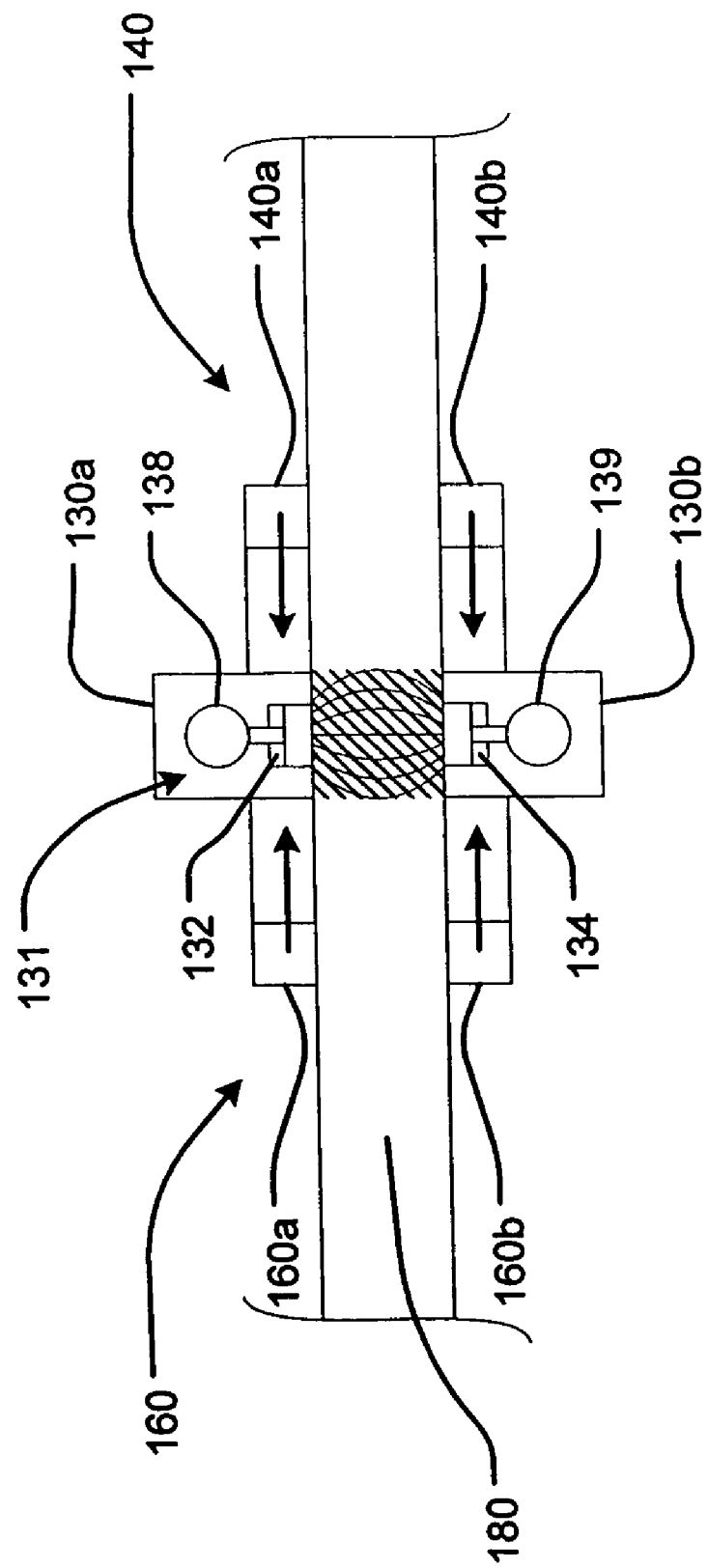
FIG. 5 is an enlarged, side section view illustrating the electrosurgical device of FIG. 4.

Now in reference to FIGS. 4 and 5, a tissue 180, such as, a tendon or ligament is shown positioned between the forceps 130 and the first and second clamps 140, 160 of the electrosurgical device 100. More particularly, the tissue 180 is shown positioned between the first and second arms 130a, 130b of the forceps 130. Similarly, the tissue 180 is shown positioned between the first and second jaws 140a, 140b of the first clamp 140 and the first and second jaws 160a, 160b of the second clamp 160. As discussed above, the operator of the electrosurgical device 100 can selectively energize the heat delivery modality 110 to provide thermal energy to the tissue treatment zone. In the illustrated embodiment, the operator of the electrosurgical device 100 can selectively energize the electrode arrangement 131 (e.g., the first and second electrodes 132, 134) to induce an electric current through the tissue 180 being treated or, more particularly, the treatment zone. As used herein, the phrase "treatment zone" generally refers to the portion or area of the tissue 180 located adjacent to and/or substantially between the first and second arms 130a, 130b of the forceps 130. In the illustrated embodiment, the thermal energy passes through the treatment zone as shown by the dotted lines in FIG. 5.

The thermal energy causes the tissue 180 within the treatment zone to contract or shrink. As discussed above, it is typically desirable to allow the surgeon or operator of the electrosurgical device 100 to control the shrinkage of the tissue 180. Existing electrosurgical devices monitor the temperature at or near the treatment zone to allow the surgeon to control the thermal energy introduced to the tissue treatment zone. The electrosurgical device 100 of the present disclosure, however, allows the operator to precisely control the thermal energy being introduced to the tissue treatment zone by monitoring the shrinkage of the tissue 180 being treated. Accordingly, the shrinkage of the tissue 180 being treated can be more precisely controlled.

To accomplish this, the sensor arrangement 112 is configured to engage or contact the tissue 180, thereby, sensing or detecting the shrinkage or contraction of the tissue 180 as thermal energy is introduced to the tissue treatment zone. For example, in the illustrated embodiment, the first and second clamping members 140, 160 are shown in engagement with the tissue 180 outside of the tissue treatment zone. In this embodiment, the first clamp 140 is preferably pivotably connected to the main body 102 at or near a pivot position 152. As a result, the first clamp 140 is able to rotate about the pivot position 152 such that the upper flange 144 (FIG. 2) moves inwardly towards the forceps 130. By "inwardly," it is generally meant that the first clamp 140 moves leftward and towards the forceps 130 such that the lateral distance $D_L$ (FIG. 2) between the first clamp 140 and the forceps 130 is reduced. Similarly, the second clamp 160 is preferably pivotably connected to the main body 102 at or near a pivot position 172. As a result, the second clamp 160 is able to rotate about the pivot position 172 such that the upper flange 164 moves inwardly towards the forceps 130. By "inwardly," it is generally meant that in the orientation shown in FIG. 2, the second clamp 160 moves rightward and towards the forceps 130 such that the lateral distance $D_L$ (FIG. 2) between the second clamp 160 and the forceps 130 is reduced. While the first and second clamps 140, 160 are pivotably connected to the main body 102, one skilled in the art will readily appreciate that the first and second clamps 140, 160 can be slidably connected to the main body 102 so that they are able to slide back and forth relative to the expansion and/or contraction of the tissue 180 being treated.

As a result of this configuration, the electrosurgical device 100 is able to detect a change in dimension of the tissue 180 being treated as thermal energy is introduced to the treatment zone. In particular, in the illustrated embodiment, the electrosurgical device 100 is able to detect the shrinkage or contraction of the tissue 180 being treated as thermal energy is introduced to the treatment zone. Furthermore, the electrosurgical device 100 is able to detect the recovery or expansion of the tissue 180 being treated as the thermal energy (e.g., heat) is removed from the treatment zone. In a preferred embodiment, the electrosurgical device 100 also can include a displacement measurement device 174 for measuring the change in dimension of the tissue 180, for example, the shrinkage or contraction of the tissue 180 being treated. In particular, in the illustrated embodiment, the first and second clamps 140, 160 are coupled to a displacement measurement device 174 that measures the angular or rotational displacement of the first and second clamps 140, 160 as thermal energy is introduced to the treatment zone. For example, the first and second clamps 140, 160 can be coupled to a linear potentiometer, optical sensor, spring/force sensor, or other similar displacement measurement device for measuring the angular or rotation displacement of the first and second clamps 140, 160.

The amount of change in the dimension of the tissue 180 being treated can be determined by calculating the displacement of each of the contact sensors used to engage the tissue 180. In the illustrated embodiment, the amount of shrinkage in the tissue 180 is determined by calculating the angular displacement of the first and second clamps 140, 160. Once the desired shrinkage of the tissue 180 has been achieved, the displacement measurement device 174 can provide a control signal to the electronic control unit 116 (FIG. 1) to reduce or minimize the amount of theiiiial energy being supplied to the treatment zone by regulating the power source 118 (FIG. 1). Alternatively, the first and second clamps 140, 160 can include a mechanical stop (not shown) to prevent shrinkage of the tissue beyond a pre-determined amount or percentage.

Figure 6:
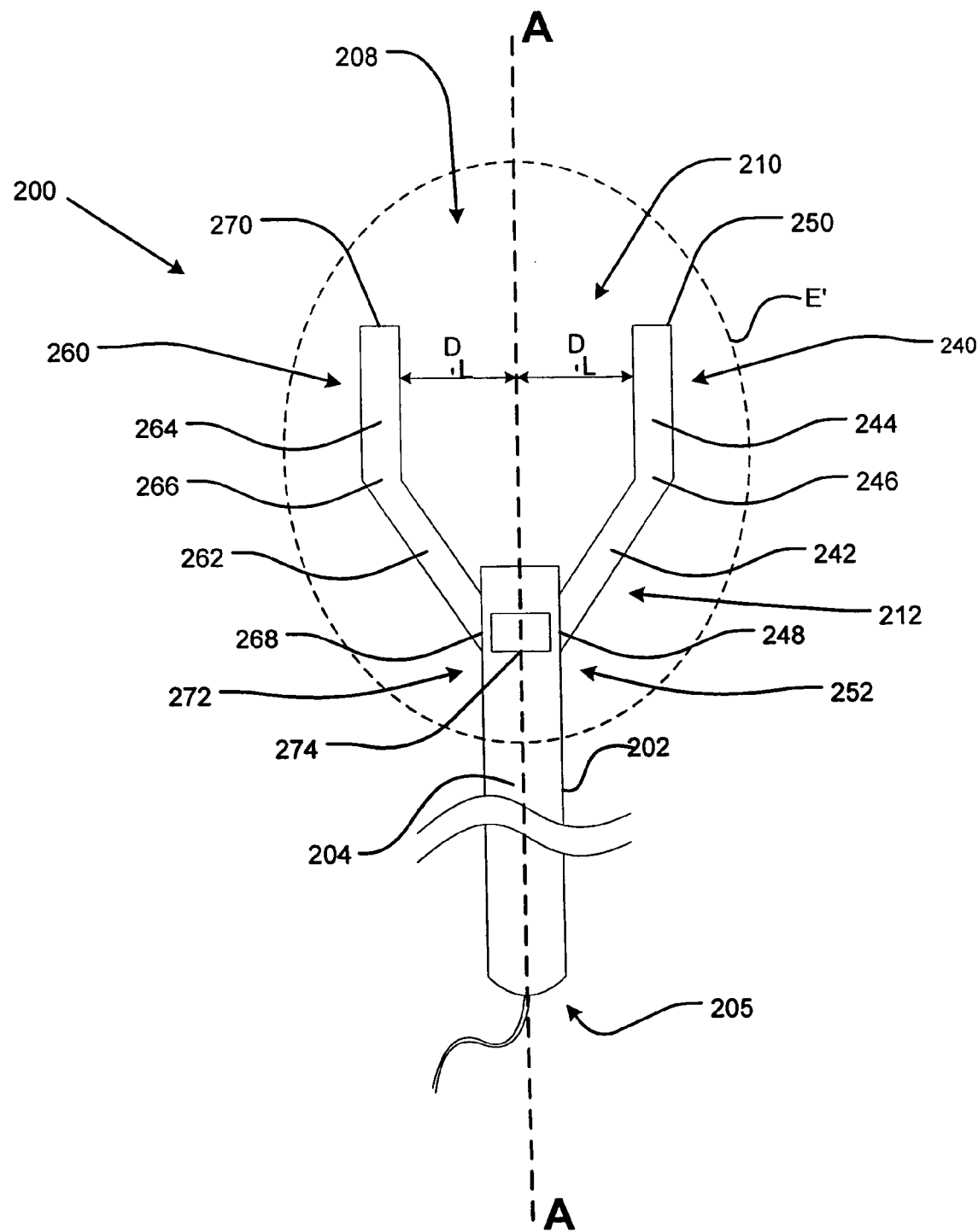
FIG. 6 is an enlarged, top view illustrating a second possible embodiment of the electrosurgical device of FIG. 1.

A second possible embodiment of a medical device for use in accordance with the principles of the present disclosure will now be described in connection with FIGS. 6-9. As shown in FIG. 6, the electrosurgical device 200 generally includes a main body 202 having a proximal end 206 and a distal end 208. The phrase "proximal end" is generally meant to refer to the portion of the electrosurgical device 200 that is held in the operator's hand during use. Conversely, the phrase "distal end" is generally meant to refer to the portion of the electrosurgical device 200 at or near a location that contacts the patient. The main body 202 can include a handle portion 204 at or near its proximal end 206 and an end effector region E' at or near its distal end 208. In the illustrated embodiment, the handle portion 204 depends downwardly along the main body portion 202 away from the end effector region E' to provide a suitable area for gripping or handling the electrosurgical device 200 during use. By "downwardly," it is generally meant that in the orientation shown in FIG. 5, the handle portion 204 extends below the end effector region E'.

In this embodiment, the end effector region E' includes a sensor arrangement 212 that is configured to engage and detect a change in dimension of the tissue being treated. The sensor arrangement 212 generally includes at least one contact sensor situated and arranged at the distal end 208 of the main body 202. Exemplary contact sensors capable of engaging and detecting a change in dimension of the tissue being treated include, but are not limited to, clamping members, needles, or other devices that can grasp or embed within the tissue being treated. While many embodiments of the sensor arrangement 212 are contemplated, in the illustrated embodiment, the sensor arrangement 212 includes a first clamp 240 and a second clamp 260 situated and arranged astride the main body 202.

Figure 7:
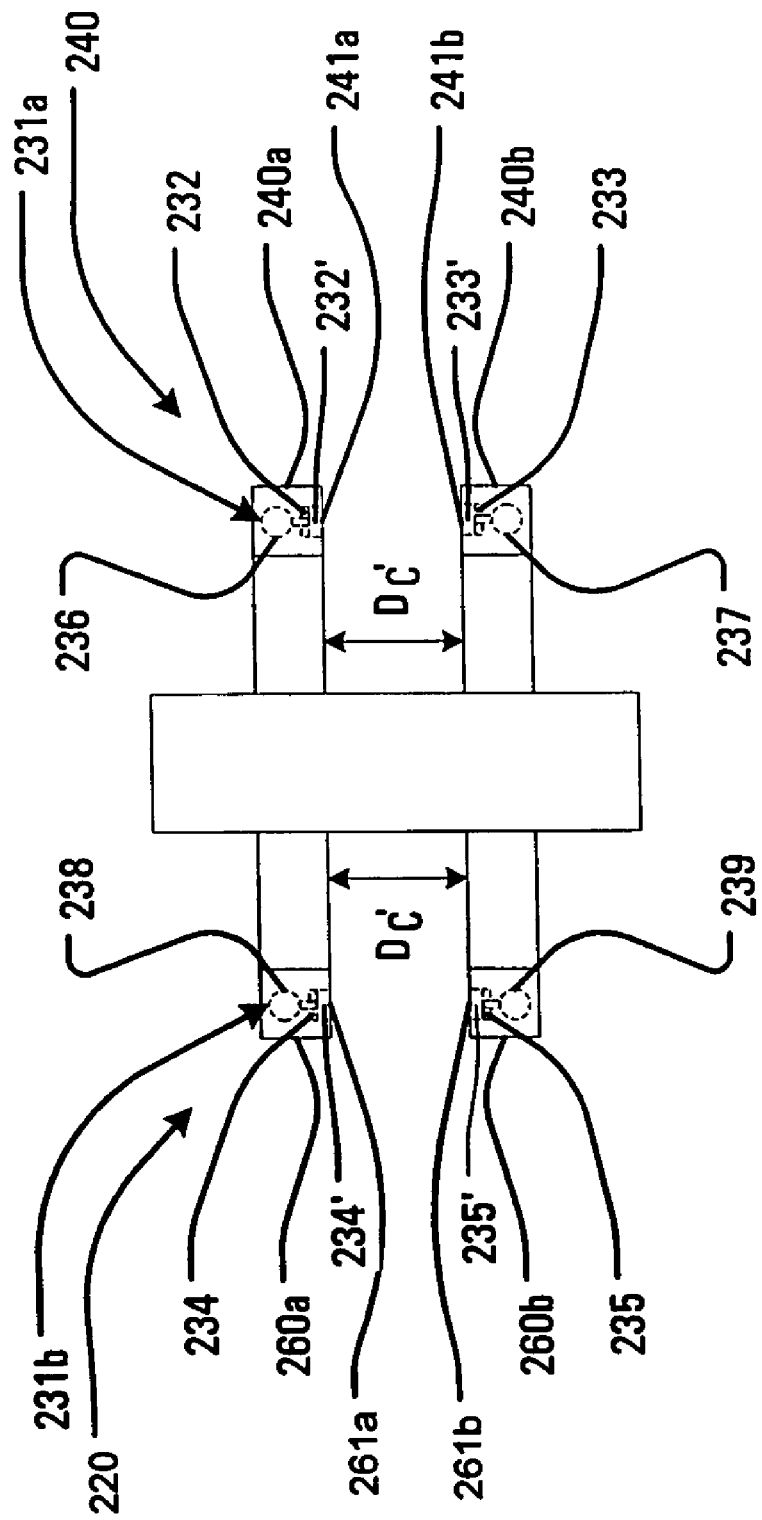
FIG. 7 is an enlarged, side section view illustrating the electrosurgical device of FIG. 6 having a sensor for detecting a change in tissue dimension.

As shown in FIG. 7, the first clamp 240 can comprise first and second symmetrical jaw members 240a, 240b. Each of the jaw members 240a, 240b include a lower arm member 242 (FIG. 6) extending away from the main body portion 202 of the device 200 and an upper flange member 244 (FIG. 6). In this embodiment, an elbow or shoulder 246 (FIG. 6) is defined by the intersection of the lower arm member 242 and the upper flange 244. The first and second symmetrical jaw members 240a, 240b also include a proximal end portion 248 (FIG. 6) and a distal end portion 250 (FIG. 6). The phrase "proximal end portion" is generally meant to refer to the portion of each of the first and second jaw members 240a, 240b at or near their point of attachment to the main body 202. Likewise, the phrase "distal end portion" is generally meant to refer to the portion of each of the first and second jaw members 240a, 240b at or near a location furthest from their point of attachment to the main body 202.

Similarly, the second clamp 260 can comprise first and second symmetrical jaw members 260a, 260b. Each of the jaw members 260a, 260b include a lower arm member 262 (FIG. 6) extending away from the main body portion 202 of the device 200 and an upper flange member 264 (FIG. 6). In this embodiment, an elbow or shoulder 266 (FIG. 6) is defined by the intersection of the lower arm member 262 and the upper flange 264. Each of the jaw members 260a, 260b comprising the second clamp 260 also include a proximal end portion 268 (FIG. 6) and a distal end portion 270 (FIG. 6). As with the first clamp 240 discussed above, the phrase "proximal end portion" is generally meant to refer to the portion of the second clamp 260 at or near it point of attachment to the main body 202. Similarly, the phrase "distal end portion" is generally meant to refer to the portion of each of the jaw members 260a, 260b at or near a location furthest from its point of attachment to the main body 202.

In the illustrated embodiment, the first and second symmetrical jaw members 240a, 240b comprising the first clamp 240 are spaced apart a distance $D_c'$ to define a passageway for receiving the tissue being treated. In one possible embodiment, the distance $D_c'$ can be selectively adjusted, thereby, increasing or decreasing the compressive forces being applied to the tissue being treated. Moreover, the first and second jaw members 240a, 240b can include inner surfaces 241a, 241b that resistively contact the tissue being treated. By "resistively contact," it is generally meant that the inner surfaces 241a, 241b are textured such that the first clamp 240 maintains a grasp on the tissue being treated. For example, the inner surfaces 241a, 241b can include serrations, grooves, or any other similar surface roughness that increase the friction between the first clamp 240 and the tissue being treated.

Similarly, the first and second symmetrical jaw members 260a, 260b comprising the second clamp 260 are spaced apart a distance $D_c'$ to define a passageway for receiving the tissue being treated. As discussed above in connection with the first clamp 240, in one possible embodiment, the distance $D_c'$ can be selectively adjusted to increase or decrease the compressive forces being applied to the tissue being treated. Moreover, the first and second jaw members 260a, 260b comprising the second clamp 260 can include inner surfaces 261a, 261b that resistively contact the tissue being treated. By "resistively contact," it is generally meant that the inner surfaces 261a, 261b are textured such that the second clamp 260 maintains a grasp on the tissue being treated. For example, the inner surfaces 261a, 261b can include serrations, grooves, or any other surface roughness that increase the friction between the second clamp 260 and the tissue being treated.

As with the first embodiment discussed above, the end effector region E' includes a heat delivery modality 210 for providing thermal energy to the tissue being treated. While many embodiments of the heat delivery modality 210 are contemplated, in the illustrated embodiment, the heat delivery modality 210 includes an electrode arrangement for providing thermal energy to the tissue being treated. In particular, as shown in FIG. 7, the heat delivery modality 210 can include a first electrode arrangement 231a operable with the first clamp 240 and a second electrode arrangement 231b operable with the second clamp 260. The first electrode arrangement 231a includes a first electrode 232 at the first jaw member 240a of the first clamp 240 and a second electrode 233 at the second jaw member 240b. Similarly, the second electrode arrangement 231b includes a first electrode 234 at the first jaw member 260a of the second clamp 260 and a second electrode 235 at the second jaw member 260b. In one possible embodiment, the first and second electrodes 232, 233 at the first clamp 240 and the first and second electrodes 234, 235 at the second clamp 260 can be selectively energized to provide electrical energy to the tissue being treated. In a preferred embodiment, the thermal energy provided to the tissue being treated is RF energy.

In the embodiment illustrated in FIG. 7, the first and second jaw members 240a, 240b of the first clamp 240 is preferably provided with a solution delivery channel. In particular, a first solution delivery channel 236 is provided within the first jaw member 240a and a second solution delivery channel 237 is provided within the second jaw member 240b. The solution delivery channels 236, 237 provide a path for fluid communication between a fluid source (not shown) and the first clamp 240. Specifically, the solution delivery channel 236 provides a path for fluid communication between a fluid source and the first jaw member 240a and the solution delivery channel 237 provides a path for fluid communication between a fluid source and the second jaw member 240b. Fluid can flow from the solution delivery channel 236 through small holes (not shown) in the first electrode 232 (at the first clamp 240) and into a region 232' located between the first electrode 232 and the tissue (not shown). Similarly, fluid can flow from the solution delivery channel 237 through small holes (not shown) in the second electrode 233 (at the first clamp 240) and into a region 233' located between the second electrode 233 and the tissue.

Similarly, the first and second jaw members 260a, 260b of the second clamp 260 is preferably provided with a solution delivery channel. In particular, a first solution delivery channel 238 is provided within the first jaw member 260a and a second solution delivery channel 239 is provided within the second jaw member 260b. The solution delivery channels 238, 239 provide a path for fluid communication between a fluid source (not shown) and the second clamp 260. Specifically, the first solution delivery channel 238 provides a path for fluid communication between a fluid source and the first jaw member 260a and the second solution delivery channel 239 provides a path for fluid communication between a fluid source and the second jaw member 260b. Fluid can flow from the solution delivery channel 238 through small holes (not shown) in the first electrode 234 (at the second clamp 260) and into a region 234' located between the first electrode 234 and the tissue (not shown). Similarly, fluid can flow from the solution delivery channel 239 through small holes (not shown) in the second electrode 235 (at the second clamp 260) and into a region 235' located between the second electrode 233 and the tissue. In providing the solution delivery channels 236, 237, 238, 239, the electrosurgical device 200 of the present disclosure is able to introduce a conductive fluid, such as, a saline solution or other similar electrolytic solution, at the electrode/tissue interface to minimize the amount of tissue damage, char formation, smoke generation or other similar damage to the tissue being treated.

Figure 8:
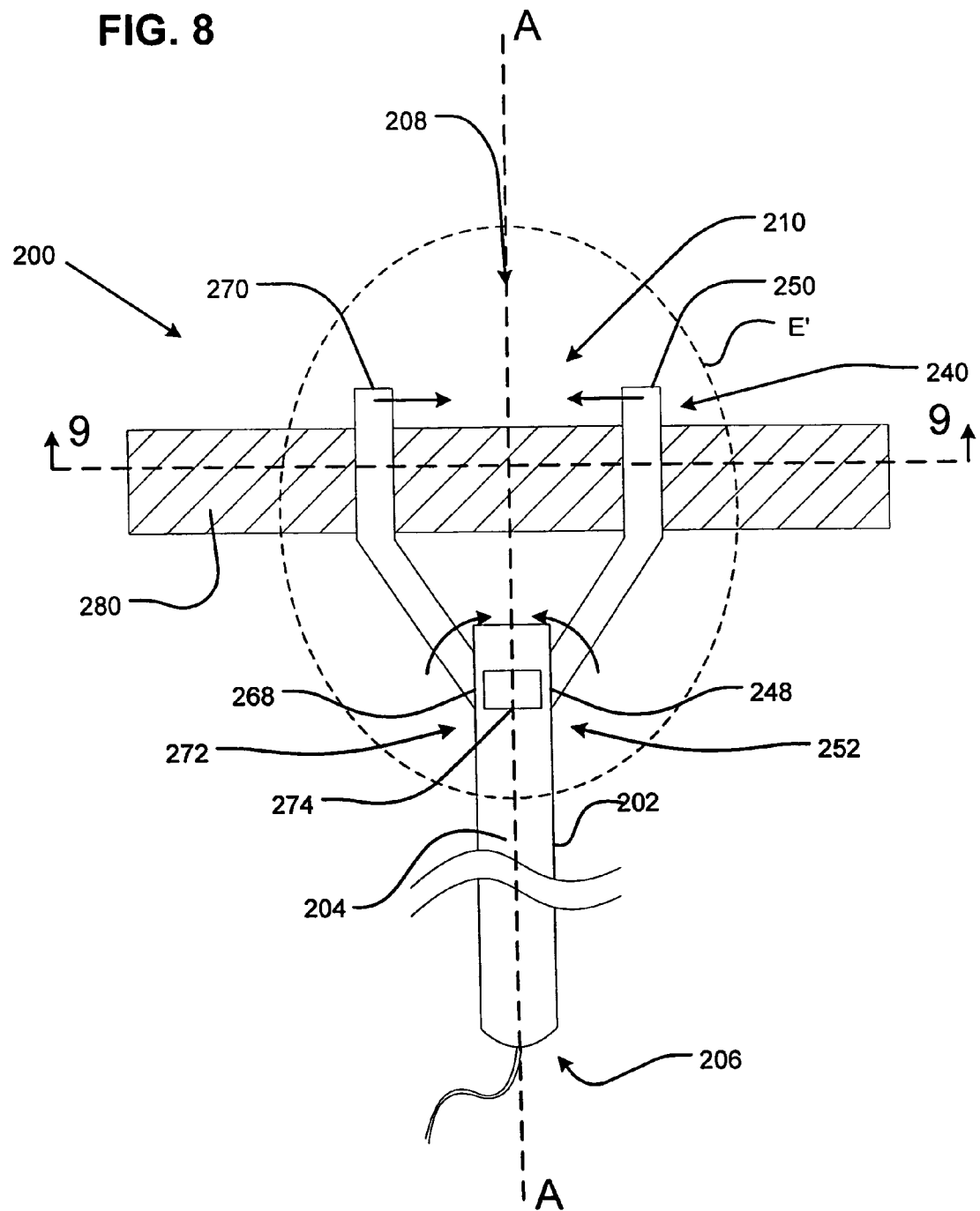
FIG. 8 is an enlarged, a top view illustrating the electrosurgical device of FIG. 6 having a tissue positioned within the device.
Figure 9:
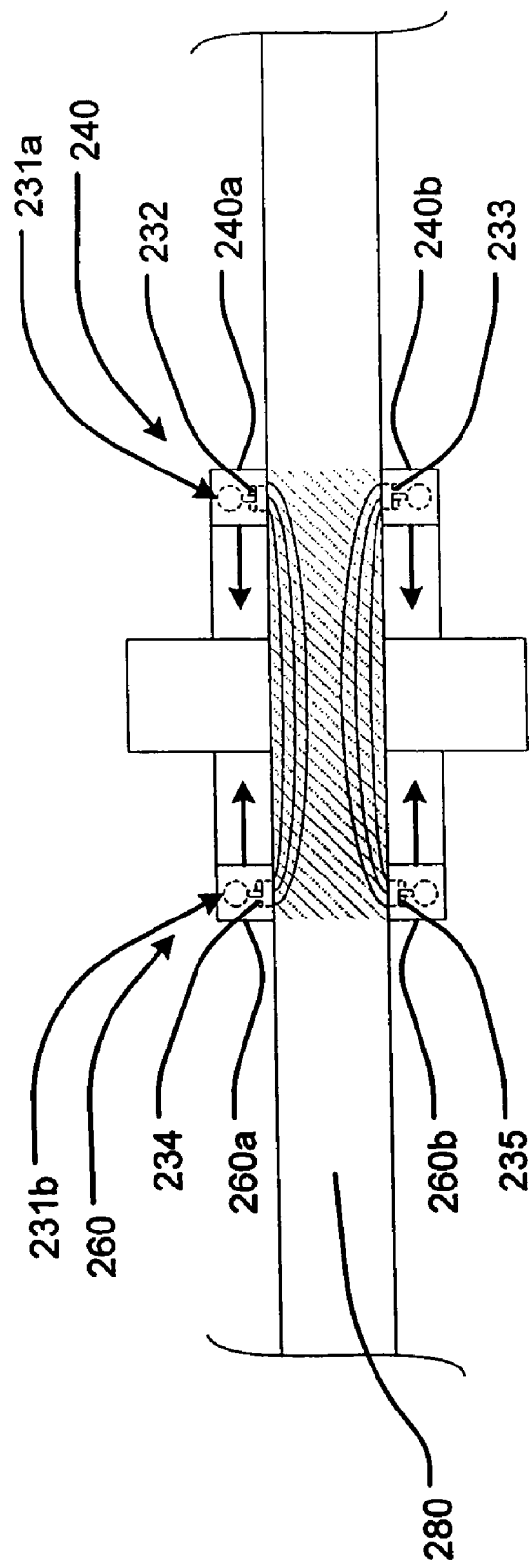
FIG. 9 is an enlarged, side section view illustrating the electrosurgical device of FIG. 8.

Now in reference to FIGS. 8 and 9, a tissue 280 such as, a tendon or ligament is shown positioned between the first and second clamps 240, 260 of the electrosurgical device 200. More particularly, the tissue 280 is shown positioned between the first and second jaws 240a, 240b of the first clamp 240 and the first and second jaws 260a, 260b of the second clamp 260. As discussed above, the operator of the electrosurgical device 200 can selectively energize the first and second electrodes 232, 233 situated at the first clamp 240 and the first and second electrode 234, 235 situated at the second clamp 260 to provide thermal energy to the tissue 280 being treated or, more particularly, the treatment zone. As used herein, the phrase "treatment zone" generally refers to the portion or area of the tissue 280 located adjacent to and/or substantially between the first and second clamps 240, 260. In the illustrated embodiment, thermal energy passes through the treatment zone as shown by the dashed lines in FIG. 9.

The thermal energy causes the tissue 280 within the treatment zone to contract or shrink. As with the first embodiment disclosed above, the electrosurgical device 200 allows the operator to precisely control the thermal energy being introduced to the tissue treatment zone by monitoring the shrinkage of the tissue 280 being treated. Accordingly, the shrinkage of the tissue 280 can be more precisely controlled.

To accomplish this, the sensor arrangement 212 is configured to engage or contact the tissue 280, thereby, sensing or detecting the shrinkage or contraction of the tissue 280 as thermal energy is introduced to the treatment zone. For example, in the illustrated embodiment, the first and second clamping members 240, 260 are shown in engagement with the tissue 280. In this embodiment, the first clamp 240 is preferably pivotably connected to the main body 202 at or near a pivot position 252. As a result, the first clamp 240 is able to rotate about the pivot 252 such that the upper flange 244 (FIG. 6) moves inwardly towards a reference axis A-A extending upwards from the main body 202 as shown in FIG. 6. By "inwardly," it is generally meant that the first clamp 240 moves leftward and towards the reference axis A-A such that the lateral distance $D'_L$ between the first clamp 240 and the reference axis A-A is reduced. Similarly, the second clamp 260 is preferably pivotably connected to the main body 202 at or near a pivot position 272. As a result, the second clamp 260 is able to rotate about the pivot 272 such that the upper flange 264 moves inwardly towards the reference axis A-A. By "inwardly," it is generally meant that in the orientation shown in FIG. 5, the second clamp 260 moves rightward and towards the reference axis A-A such that the lateral distance $D'_L$ between the second clamp 260 and the reference axis is reduced.

As a result of this configuration, the electrosurgical device 200 is able to detect a change in dimension of the tissue 280 being treated as thermal energy is introduced to the treatment zone. In particular, in the illustrated embodiment, the electrosurgical device 200 is able to detect the shrinkage or contraction of the tissue 280 being treated as thermal energy is introduced to the treatment zone. Furthermore, the electrosurgical device 200 is able to detect the recovery or expansion of the tissue 280 being treated as the thermal energy (e.g., heat) is removed from the treatment zone. In a preferred embodiment, the electrosurgical device 200 also can include a displacement measurement device 274 for measuring the shrinkage or contraction of the tissue 280 being treated. In particular, the first and second clamps 240, 260 are coupled to a displacement measurement device 274 that measures the angular or rotational displacement of the first and second clamps 240, 260 as thermal energy is introduced to the treatment zone. For example, the first and second clamps 240, 260 can be coupled to a linear potentiometer, optical sensor, spring/force sensor, or other similar sensing device for measuring the angular or rotation displacement of the first and second clamps 240, 260.

The amount of shrinkage or contraction in the tissue 280 can be determined by calculating the displacement of each contact sensors used to engage and detect shrinkage of the tissue 280. In the illustrated embodiment, the amount of shrinkage in the tissue 280 is determined by calculating the angular displacement of the first and second clamps 240, 260. Once the desired shrinkage of the tissue 280 has been achieved, the displacement measurement device 274 can provide a control signal to the electronic control unit 116 (FIG. 1) to reduce or minimize the amount of thermal energy being supplied to treatment zone by regulating the power source 118 (FIG. 1). Alternatively, the first and second clamps 240, 260 can include a mechanical stop (not shown) to prevent shrinkage of the tissue beyond a pre-determined amount or percentage.

Figure 10:
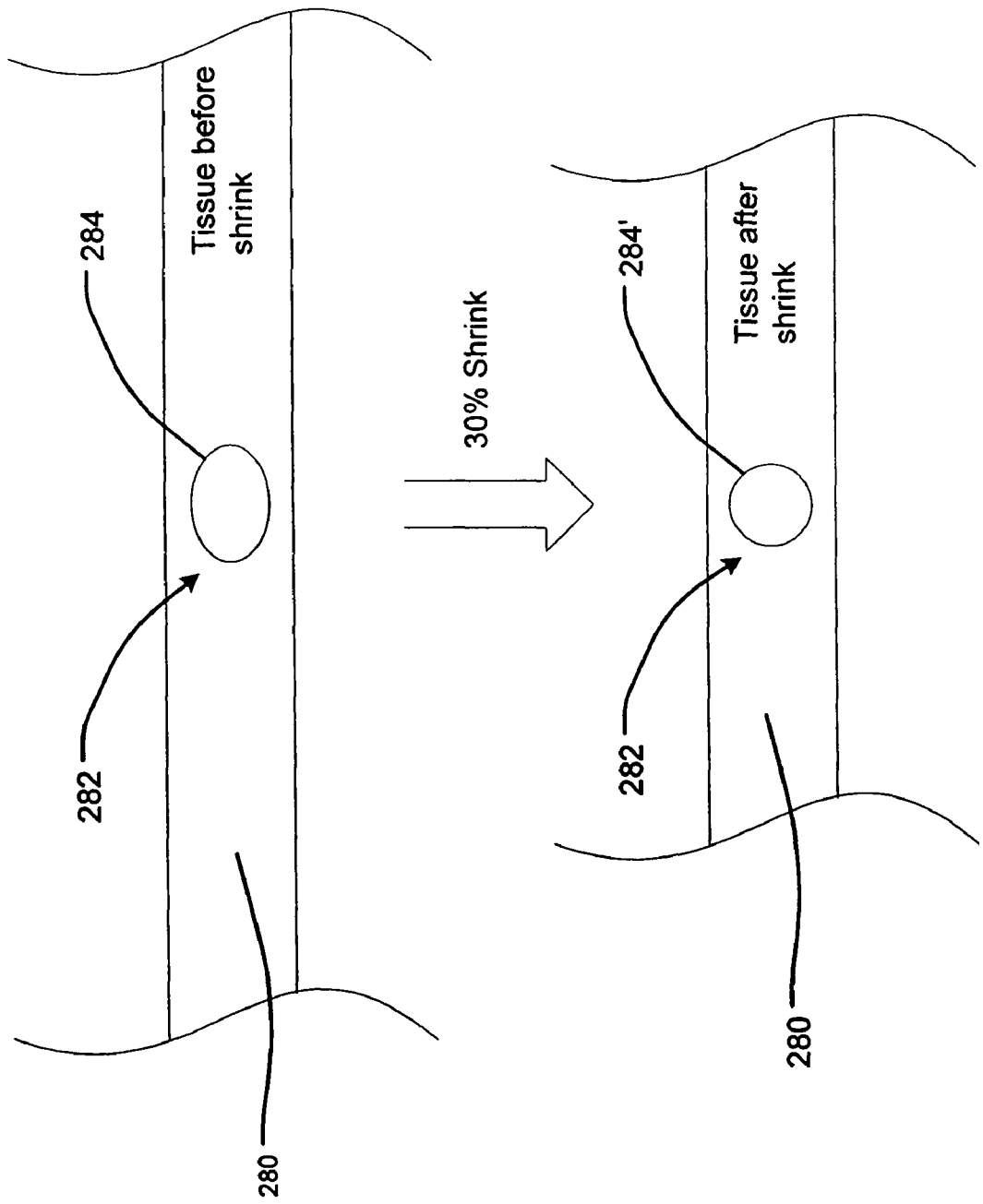
FIG. 10 illustrates an alternative configuration of the electrosurgical device of FIG. 1 for measuring change in tissue dimension in accordance with the present disclosure.

As an alternative to using a sensor arrangement to detect a change in dimension in the tissue being treated, a visual indicator can be used to allow the operator or surgeon to visually detect the shrinkage or contraction of the tissue being treated. For example, as shown in FIG. 10, a visual indicator 282 can be used to measure the shrinkage of the tissue 280. In one possible embodiment, the visual indicator 282 can be applied to the surface of the tissue 280. Preferably, the visual indicator 282 is applied to the surface of the tissue 280 between the first and second clamps 240, 260 using a nontoxic ink or other substance capable of being applied to a tissue. In so doing, the operator can visually inspect the indicator 282 as the thermal energy is being introduced into the treatment zone. In particular, as the tissue 280 shrinks due to the thermal energy being supplied to the treatment zone, the visual indicator 282 changes shape. In the illustrated embodiment, the visual indicator 282 prior to the introduction of thermal energy is an elliptical pattern 284. After the tissue 280 shrinks due to the introduction of the thermal energy, the visual indicator 282 shrinks to a circular pattern 284'. Once the visual indicator shrinks to the appropriate pattern, the operator or surgeon can reduce the amount of thermal energy being supplied by the heat delivery modality 210 by regulating the power source 118 (FIG. 1).

The various embodiments described above are provided by way of illustration only and should not be construed to limit the invention. Those skilled in the art will readily recognize the various modifications and changes which may be made to the present invention without strictly following the exemplary embodiments illustrated and described herein, and without departing from the true spirit and scope of the present invention, which is set forth in the following claims.

The claimed invention is:

1. An electrosurgical instrument having an end effector, the end effector configured to simultaneously provide radio frequency power and a fluid to treat tissue, the power sufficient to cause a dimensional change of the tissue, the end effector comprising:
   at least one electrode to deliver the radio frequency power to the tissue;
   at least one fluid outlet to deliver the fluid to the tissue;
   a dimensional change sensor configured to grasp the tissue and move relative to a dimensional change of the tissue while having a grasp of the tissue;
   wherein the dimensional change sensor comprises a first clamp having a first jaw member and a second jaw member and a second clamp having a first jaw member and a second jaw member, the first and second jaw members of the first clamp being configured in an opposing manner to grasp tissue therebetween when the first and second jaws of the first clamp are moved together, and the first and second jaw members of the second clamp being configured in to grasp tissue therebetween when the first and second jaws of the second clamp are moved together; and
   wherein the first jaw members of the first and second clamps are configured to move in correspondence with the dimensional change of the tissue, wherein the at least one electrode is disposed between either the first jaw members of the first and second clamps or the second jaw members of the first and second clamps to treat tissue grasped by the jaw members of the first and second clamps such that the dimensional change in the tissue caused by such treatment will cause a corresponding change in the distance between the first jaw members of the first and second clamps.

2. The electrosurgical instrument of claim 1 wherein:
   the dimensional change sensor is configured to provide feedback to vary the radio frequency power according to the dimensional change of the tissue.

3. The electrosurgical instrument of claim 1 wherein:
   the dimensional change sensor is configured to provide feedback to treat the tissue to a predetermined dimensional change.

4. The electrosurgical instrument of claim 1 wherein:
   the dimensional change sensor is configured to provide feedback to measure the dimensional change.

5. The electrosurgical instrument of claim 1 wherein:
   the dimensional change sensor is operatively associated with a device to provide a measurement of the dimensional change.

6. The electrosurgical instrument of claim 1 wherein:
   the dimensional change sensor is operatively associated with means to provide a measurement of the dimensional change.

7. The electrosurgical instrument of claim 1 wherein:
   the dimensional change sensor comprises a contact sensor.

8. The electrosurgical instrument of claim 1 wherein:
   the dimensional change sensor comprises a shrinkage sensor; and
   the dimension change of the tissue comprises a shrinkage of the tissue.

9. The electrosurgical instrument of claim 8 wherein:
   the shrinkage sensor is configured to move relative to the shrinkage of the tissue.

10. The electrosurgical instrument of claim 8 wherein:
    the shrinkage sensor is configured to provide feedback to vary the radio frequency power according to the shrinkage of the tissue.

11. The electrosurgical instrument of claim 8 wherein:
    the shrinkage sensor is configured to provide feedback to treat the tissue to a predetermined shrinkage.

12. The electrosurgical instrument of claim 8 wherein:
    the shrinkage sensor is configured to provide feedback to measure the shrinkage.

13. The electrosurgical instrument of claim 8 wherein:
    the shrinkage sensor is operatively associated with a device to provide a measurement of the shrinkage.

14. The electrosurgical instrument of claim 8 wherein:
    the shrinkage sensor is operatively associated with means to provide a measurement of the shrinkage.

15. The electrosurgical instrument of claim 1 further comprising:
    a monopolar electrosurgical instrument.

16. The electrosurgical instrument of claim 1 further comprising:
    a bipolar electrosurgical instrument.

17. The electrosurgical instrument of claim 1 wherein:
    the at least one fluid outlet is positioned to provide the fluid onto the at least one electrode.

18. The electrosurgical instrument of claim 1 wherein:
    the at least one fluid outlet is at least partially defined by the at least one electrode.

19. The electrosurgical instrument of claim 1 wherein:
    the at least one fluid outlet is at least partially defined by a hole in the at least one electrode.

20. The electrosurgical instrument of claim 1 wherein:
    the at least one fluid outlet is configured to provide the fluid to wet the at least one electrode.

21. The electrosurgical instrument of claim 1 wherein:
    the at least one electrode comprises a plurality of electrodes.

22. The electrosurgical instrument of claim 1 wherein:
    the at least one fluid outlet comprises a plurality of fluid outlets.

23. The electrosurgical instrument of claim 1 wherein:
    the at least one electrode comprises a first electrode and a second electrode; and the at least one fluid outlet comprises a first fluid outlet and a second fluid outlet.

24. The electrosurgical instrument of claim 23 wherein:
the first fluid outlet is positioned to provide the fluid onto the first electrode; and the second fluid outlet is positioned to provide the fluid onto the second electrode.

25. The electrosurgical instrument of claim 23 wherein:
the first fluid outlet is configured to provide the fluid to wet the first electrode; and the second fluid outlet is configured to provide the fluid to wet the second electrode.

26. The electrosurgical instrument of claim 1 wherein:
wherein the second jaw members of the first and second clamps are configured to move in correspondence with the dimensional change of the tissue, wherein the dimensional change in the tissue will cause a corresponding change in the distance between the second jaw members of the first and second clamps.

27. The electrosurgical instrument of claim 1 wherein:
a distance between the first and second jaw member of the first clamp is selectively adjustable to either increase or decrease a compressive force applied to the tissue being treated, and
a distance between the first and second jaw member of the second clamp is selectively adjustable to either increase or decrease a compressive force applied to the tissue being treated.

28. An electrosurgical instrument comprising:
at least one electrode;
a dimensional change sensor configured to grasp the tissue and move relative to a dimensional change of the tissue while having a grasp of the tissue;
wherein the dimensional change sensor comprises a first clamp having a first jaw member and a second jaw member and a second clamp having a first jaw member and a second jaw member, the first and second jaw members of the first clamp being configured in an opposing manner to grasp tissue therebetween when the first and second jaws of the first clamp are moved together, and the first and second jaw members of the second clamp being configured in an opposing manner to grasp tissue therebetween when the first and second jaws of the second clamp are moved together; and
wherein the first jaw members of the first and second clamps are configured to move in correspondence with the dimensional change of the tissue, wherein the at least one electrode is disposed between either the first jaw members of the first and second clamps or the second jaw members of the first and second clamps to treat tissue grasped by the jaw members of the first and second clamps such that the dimensional change in the tissue caused by such treatment will cause a corresponding change in the distance between the first jaw members of the first and second clamps.

29. The electrosurgical instrument of claim 28 further comprising:
at least one fluid outlet positioned to provide a fluid onto the at least one electrode.

30. The electrosurgical instrument of claim 28 wherein:
a distance between the first and second jaw members of the first clamp is selectively adjustable to either increase or decrease a compressive force applied to the tissue being treated, and
a distance between the first and second jaw members of the second clamp is selectively adjustable to either increase or decrease a compressive force applied to the tissue being treated.

31. The electrosurgical instrument of claim 28 wherein:
wherein the second jaw members of the first and second clamps are configured to move in correspondence with the dimensional change of the tissue, wherein the dimensional change in the tissue will cause a corresponding change in the distance between the second jaw members of the first and second clamps.

* * * * *